United States Patent [19]

Fritzberg et al.

[11] Patent Number: 5,606,028

[45] Date of Patent: Feb. 25, 1997

[54] ANCHIMERIC RADIOMETAL CHELATING COMPOUNDS

[75] Inventors: Alan R. Fritzberg, Edmonds; Ananthachari Srinivasan, Kirkland, both of Wash.

[73] Assignee: NeoRx Corporation, Seattle, Wash.

[21] Appl. No.: 532,041

[22] Filed: Sep. 21, 1995

Related U.S. Application Data

[63] Continuation of Ser. No. 221,987, Apr. 1, 1994, abandoned, which is a continuation of Ser. No. 968,048, Oct. 28, 1992, abandoned, which is a division of Ser. No. 157,284, Feb. 17, 1988, Pat. No. 5,202,451.

[51] Int. Cl.$^6$ .................. C07K 17/02; A61K 51/08; A61K 51/10

[52] U.S. Cl. ............ 530/391.5; 530/345; 530/391.1; 530/391.3; 530/404; 530/405; 530/408; 530/409

[58] Field of Search ............... 530/345, 391.1, 530/391.3, 391.5, 404, 405, 408, 409; 424/1.49, 1.53, 1.69

[56] References Cited

U.S. PATENT DOCUMENTS

| | | | |
|---|---|---|---|
| 3,910,988 | 10/1975 | Jones et al. | 260/471 |
| 3,974,268 | 8/1976 | Subramanian et al. | 424/1 |
| 4,027,005 | 5/1977 | Adler et al. | 424/1 |
| 4,232,000 | 11/1980 | Fawzi | 424/1 |
| 4,233,285 | 11/1980 | Winchell et al. | 424/1 |
| 4,421,735 | 12/1983 | Haber et al. | 424/1.1 |
| 4,434,151 | 2/1984 | Byrne et al. | 424/1.1 |
| 4,444,690 | 4/1984 | Fritzberg | 260/429 |
| 4,444,743 | 4/1984 | Yokoyama et al. | 424/1.1 |
| 4,454,106 | 6/1984 | Gansow et al. | 424/1.1 |
| 4,571,430 | 2/1986 | Byrne et al. | 560/148 |
| 4,575,556 | 3/1986 | Byrne et al. | 549/63 |
| 4,673,562 | 6/1987 | Davison et al. | 424/1.1 |
| 4,849,511 | 7/1989 | Verbruggen | 534/14 |
| 4,861,869 | 8/1989 | Nicolotti et al. | 530/402 |
| 4,897,255 | 1/1990 | Fritzberg et al. | 424/1.1 |
| 5,202,451 | 4/1993 | Fritzberg et al. | 556/419 |

FOREIGN PATENT DOCUMENTS

| | | |
|---|---|---|
| 0108406 | 5/1984 | European Pat. Off. . |
| 0135160 | 6/1984 | European Pat. Off. . |
| 0137457 | 4/1985 | European Pat. Off. . |
| 0163119 | 12/1985 | European Pat. Off. . |
| 0173629 | 3/1986 | European Pat. Off. . |
| 0188256 | 7/1986 | European Pat. Off. . |
| 0200492 | 12/1986 | European Pat. Off. . |
| 0250013 | 12/1987 | European Pat. Off. . |

OTHER PUBLICATIONS

Oncoscint CR/OV Package Insert, 1992.
Friedman et al., Hematology/Onc. Clinics of North Amer., 4:1069–1078.
Schroff et al., Antibod. Immunoconj. and Radiopharm., 3:99–110.
Breitz et al., J. Nucl. Med., 34:908–917, 1993.
Thorpe, from "Monoclonal Antibodies '84: Biological and Clinical Applications" Ed. A. Pinchera et al., Editrice Kurtis S.R.L., 1985, pp. 475–506.
Abraham et al., J. Imm. Method., 144, pp. 77–86, 1991.
Goding, "monoclonal Antibodies: Principles and Practices", pp. 133–134, Academic Press, 1986.
Pollack, S. et al., "Chelate Mediated Transfer of Iron From Transferrin to Desferrioxamine," *British J. Hematology*, pp. 231–235, 1976.

(List continued on next page.)

*Primary Examiner*—Kay K. A. Kim
*Attorney, Agent, or Firm*—Christensen O'Connor Johnson & Kindness PLLC

[57] ABSTRACT

Anchimeric chelates are disclosed which are capable of rapidly forming stable chelates with radionuclide metals at or below physiological temperature. Bifunctional anchimeric chelates having these same properties are also disclosed which are useful for radiolabeling target specific molecules such as monoclonal antibodies and fragments thereof.

25 Claims, 8 Drawing Sheets

OTHER PUBLICATIONS

Fritzberg, A. R. et al., "Chemical and Biological Studies of Tc–99m N,N'–Bis(mercaptoacetamido)ethylenediamine: A Potential Replacement for 1–131 Iodohippurate," *J. Nucl. Med*, 22:258–263, 1981.

Davison, A. et al., "A New Class of Oxotechnetium (5+) Chelate Complexes Containing a $TcON_2S_2$ Core," *Inorganic Chemistry*, vol. 20, 1981.

Fritzberg, A. R. et al., "Synthesis and Biological Evaluation of Tc–99m N,N'Bis(mercaptoacetyl)2,3–diaminopropanoate: A Potential Replacement for [$^{131}$I]o–iodohippurate," *J. Nucl. Med.*, 7:592–598, 1982.

Khaw, B. A. et al., "Technetium–99m Labeling of Antibodies to Cardiac Myosin Fab and to Human Fibrinogen," *J. Nucl. Med*, 23:1011–1019, 1982.

Schneider, R. F. et al., "N,N'–bis(S–Benzoylmercaptoacetamido) Ethylene–diamine and Propylenediamine Ligands as Renal Function Imaging Agents. I. Alternate Synthetic Methods," *J. Nucl. Med.*, 25:223–229, 1984.

Fritzberg, A. R., "Current Status of Renal Radiopharmaceuticals," *J. Nuc. Med. Tech.*, 12:177–188, 1984.

Childs, R. L. et al., "Optimum Conditions for Labeling of DTPA–Coupled Antibodies with Technetium–99m," *J. Nucl. Med.*, 26:293–299, 1985.

Robison, T. W. et al, "Side Arm Participation in Crown Phosphonate Monoethyl Ester–Alkali Metal Cation Complexes," *J. Chem. Soc., Chem, Commun.*, pp. 990–991, 1985.

Paik, C. H. et al., "The Labeling of High Affinity Sites of Antibodies with $^{99m}$Tc," *Int. J. Nucl. Med. Biol.*, 12:3–8, 1985.

Frizberg, A. R. et al., "Synthesis and Biological Evaluation of Technetium–99m $MAG_3$ as a Hippuran Replacement," *J. Nucl. Med*, 27:111–116, 1986.

Fritzberg, A. R., "Advances in $^{99m}$Tc–Labelling of Antibodies," presented at the Symposium on Monoclonal Antibodies in Nuclear Medicine, in Freiburg i. Br., May 1–3, 1986.

Arano, Y. et al., "Synthesis and Evaluation of a New Bifunctional Chelating Agent for $^{99m}$Tc Labeling Proteins: p–Carboxy–ethyphenylglyoxal–di(N–methylthiosemicarbazone)," *Int. J. Nucl. Med Biol.*, 12:425–430, 1986.

Byrne, E. F. et al., "Technetium–99m Bifunctional Chelating Agent–Thiolactone for Coupling to Biomolecules, $N_2S_2$ Ligand for Chelation to Technetium," Proceedings of the 30th Annual Meeting, *J. Nucl. Med.*

Kasina, S. et al., "Tissue Distribution Properties of Technetium–99m–Diamide–Dimercaptide Complexes and Potential Use as Renal Radiopharmaceuticals," *J. Med. Chem.*, 29:1933–1940, 1986.

Burchiel, S. W. et al., "Biodistribution and Pharmacokinetic Analyses of Tc99m–Metallothionein Conjugated B72.3 Antibodies in Rhesus Monkeys," *J. Nucl. Med.*, 27:896, 1986.

Kasina et al., "Application of Diamide Dimercaptide $N_2S_2$ Bifunctional Chelating Agents for $^{99m}$Tc Labeling of Proteins," *Proc. Intl. Radio. Chem. Symp.*, 269–271, 1986.

European Search Report EP 89 30 1590.

Efange, S. M. N. et al., "Technetium–99m bis(Aminoethanethiol) Complexes with Amine Sidechains—Potential Brain Perfusion Imaging Agents for SPECT," *J. Nucl. Med*, 28(6), 1987.

ANCHIMERIC RADIOMETAL CHELATING COMPOUNDS

This application is a continuation application based on prior application Ser. No. 08/221,987, filed on Apr. 1, 1994, now abandoned, which is a continuation application based on prior application Ser. No. 07/968,048, filed on Oct. 28, 1992, now abandoned, which was a divisional of prior application Ser. No. 07/157,284, filed Feb. 17, 1988, now U.S. Pat. No. 5,202,451, issued Apr. 13, 1993.

TECHNICAL FIELD

This invention relates generally to chelating compounds which form complexes with metals such as radionuclide metals. Proteins such as antibodies may be radiolabeled by attaching the metal chelate compound thereto. The chelating compounds are useful for producing radiodiagnostic and radiotherapeutic agents.

BACKGROUND OF THE INVENTION

Radiolabeled chelating compounds are useful both as medical diagnostic and therapeutic agents. For example, radiolabeled ethylenediamine tetraacetic acid (EDTA), and diethylenetriaminepentaacetate (DTPA) have been reported to be useful in evaluating renal functions, Klingensmith et al., *J. Nucl. Med.* 23:377 (1982). Similarly, Kasina et al., *J. Med. Chem.* 29:1933 (1986) report promising renal pharmaceuticals that are technetium chelates of $N_2S_2$ diamido dimercaptides. Many other radiolabeled diagnostic chelates have been reported and include: tartrate and orthophosphate, Molinski et al., U.S. Pat. No. 3,987,1571 propylene amine oxime, Troutner et al., U.S. Pat. No. 4,615,876; polyhydroxycarboxylic acids, Adler et al., U.S. Pat. No. 4,027,005; organotrisubstituted trivalent phosphorus compounds, Dean et al., U.S. Pat. No. 4,582,700; bis-thiosemicarbazone, Vedee et al., U.S. Pat. No. 4,564,472; gentisyl alcohol in combination with phosphonates, Fawzi, U.S. Pat. No. 4,232,000; mercaptoacetylglycylglycylglycine ($MAG_3$) Fritzberg et al., *J. Nucl. Med.* 27:111–116 (1986); mercaptocarboxylic acids, Winchell et al., U.S. Pat. No. 4,233,285; thiosaccharides, Kubiatowicz et al., U.S. Pat. No. 4,208,398; homocysteine and homocysteinamide derivatives, Byrne et al., U.S. Pat. No. 4,571,430; metallothionein, Tolman, European application Apr. 10, 1984 0 137 457 AZ; isonitrile, Jones et al., U.S. Pat. No. 4,452,774; and imidodiphosphonate, Subramanian et al., U.S. Pat. No. 3,974,268.

One class of such compounds is the bifunctional chelating compounds, which have a functional group capable of binding a metal and a functional group reactive with a carrier molecule. Compounds of this type are being actively investigated since they are capable of stably linking radionuclides to target-specific biological molecules such as proteins, antibodies, and antibody fragments.

Diagnostic imaging of specific target tissue in vivo with a radiometal-chelate-antibody conjugate was reported by Khaw et al., *Science* 209:295 (1980). Similarly, the therapeutic use of radiometal-chelate-antibody conjugates to treat cellular disorders is disclosed by Gansow et al., U.S. Pat. No. 4,454,106.

The procedure employed to insert a radiometal into a chelating compound depends on the chemistry of the radiometal and the chemical structure of the chelating compound. A variety of radiometals can be incorporated into both simple and bifunctional chelating compounds. The particular radiometal selected depends on the intended application and availability, as well as other factors.

Generally, radiometals intended for use as therapeutic agents are alpha, beta, or Auger electron emitters, such as $^{109}Pd$, $^{111}Ag$, $^{119}Sb$, $^{198}Au$, $^{199}Au$, $^{67}Cu$, $^{105}Rh$, $^{186}Re$, $^{188}Re$, and $^{212}Bi$. Radiometals intended for use as diagnostic agents are usually positron or gamma photon emitters. For example, in positron emission tomography $^{43}Sc$, $^{44}Sc$, $^{52}Fe$, $^{55}Co$, and $^{68}Ga$ can be employed, while for gamma camera imaging $^{203}Pb$, $^{97}Ru$, $^{197}Hg$, $^{67}Ga$, $^{201}Tl$, $^{99m}Tc$, $^{113m}In$, and $^{111}In$ are usually selected.

Many of the radiometals described above are available in oxidation states unsuitable for chelation without prior treatment. $^{99m}Tc$, for example, is available as pertechnetate ($TcO_4$) and must be reduced to a lower oxidation state before chelation can occur. This is usually accomplished by the addition of a reducing agent, such as $Sn^{+2}$ or dithionite at alkaline pH to the pertechnetate chelator mixture.

Transfer of the radiometal to the ultimate chelator is often facilitated by employing a labile or weak chelating agent (WCA) in the reaction mixture, Fritzberg et al. (1986). In the case of $^{99m}Tc$, for example, an initial complex may be formed with a WCA such as gluconate. The $^{99m}Tc$-gluconate complex forms quickly, thereby minimizing reoxidation of the $^{99m}Tc$. Heating the initial Tc-WCA complex in the presence of a strong chelating agent (SCA) results in transfer of $^{99m}Tc$ to the strong chelating agent in improved yields, compared to carrying out the reduction of pertechnetate in the presence of the strong chelator alone.

Pollack et al. *British J. Hematology*, 34:231 (1976) describe the kinetic nature of the problem of transferring metals between strong chelating agents. These authors demonstrate a significantly enhanced transfer rate when a weak chelating agent, such as nitrilotriacetate, is employed.

The need to enhance the transfer kinetics of a metal to a strong chelator is particularly important when the chelator is attached to a protein. For example, Childs et al., *J. Nucl. Med.* 26:293–299 (1985) describe the rather harsh conditions, i.e. pH 4, necessary to achieve adequate binding of a radiometal to the antibody-bound chelator. Exposure to high temperatures or extremes of pH may denature or otherwise damage the protein to which the chelating compound is attached. Examples of weak chelating agents that have been used to facilitate transfer of metals to proteins or strong chelating agents attached thereto include the polyhydroxycarboxylates, glucoheptonate, Burchiel et al., *J. Nucl. Med.* 27:896 (1986) and tartrate, Kasina et al., *Proc. Intl. Radio. Chem. Symp.* 269–71 (1986). Strong chelating agents that have been conjugated to target specific proteins include: DTPA, Childs et al. (1985); EDTA, Wieder et al., U.S. Pat. No. 4,352,751 (1982); metallothionein, Tolman, European Patent Application 0137457 (1985); bis-thiosemicarbozones, Arano et al., *Int. J. Nucl. Med. Bio.* 12:425 (1986), U.S. Pat. No. 4,287,362; and diamido dimercaptide ($N_2S_2$) Fritzberg et. al. (1986).

Even when a weak chelating agent is used to facilitate incorporation of a radiometal into a strong chelating compound, the kinetics are not always sufficient unless somewhat harsh conditions are employed. It is known, for example, that transfer of technetium from a Tc-tartrate complex to an antibody-$N_2S_2$ conjugate is slow and requires heating to 50° C. or more for an hour to effect acceptable radiometal transfer. See European Patent Application Publication No. 188,256. Heating to temperatures above 37° C. often leads to aggregation of proteins such as antibodies, as well as nonspecific labeling of the antibody itself.

Accordingly, a need exists for a chelating compound that can rapidly form stable chelates with radiometals at physiological temperatures or below. Radiolabeling of bifunctional chelators suitable for conjugation to target-specific biological molecules should be possible under conditions that preserve biological activity.

SUMMARY OF THE INVENTION

The present invention provides a chelating compound having a first site at which a complex of a radionuclide metal forms and a second site at which a chelate of the radionuclide metal forms, wherein the complex has a faster rate of formation and a lower thermodynamic stability than the chelate so that when the radionuclide metal is combined with the compound, the complex at the first site forms initially, and the radionuclide metal subsequently is transferred to the second site to form a stable chelate. The radionuclide metal may be transferred to the second site by heating the compound to a temperature of about 37° C. or below after the initial complex has formed.

In one embodiment of the invention, the chelating compound has at its first site two or more atoms chosen from oxygen, nitrogen, and phosphorous (in the form of oxides), arranged such that the atoms interact with the radionuclide metal to form a complex. In one embodiment of the invention, the chelating compound has as its second site a heteroatom chain containing at least four donor atoms chosen from sulfur, nitrogen, and oxygen, wherein coordinate covalent bonds form between each of the donor atoms and the radionuclide metal to form a chelate.

In a preferred embodiment of the invention, donor atoms of the heteroatom chain at the second site include at least one divalent sulfur atom and at least two nitrogen atoms, the sulfur atom being positioned at one terminus of the heteroatom chain, and from six to seven carbon atoms positioned so that at least two carbon atoms are located between any two of the donor atoms. One chelating compound of this invention has two nitrogen atoms and two sulfur atoms as the donor atoms. Alternatively, the chelating compound may have three nitrogen atoms and one sulfur atom as the donor atoms at the second site. It is preferred that each sulfur donor atom has a protective group attached thereto. In one embodiment of the invention, one or more of the sulfur atoms, together with a protective group attached thereto, defines a thioacetal or hemithioacetal group.

The chelating compound of this invention has a flexible divalent linker, linking the first and second sites. The linker generally comprises from two to six methylene groups or methylene equivalents in a chain.

When the chelating compound is to be attached to a protein, the chelating compound additionally possesses a conjugation group that is capable of reacting with a protein to bind the chelating compound to the protein. The conjugation group is attached through a spacer to any carbon or nitrogen atom of the chelating compound.

The invention includes a kit for producing a radiolabeled protein comprising a chelating compound defined above and a protein to be radiolabeled. Optionally, the kit may comprise the protein and the chelating compound as a conjugate. The 1protein of the kit may be any suitable target site-specific protein, such as an antibody or monoclonal antibody, or a fragment thereof.

The invention also includes a method of radiolabeling a protein comprising the steps of: reacting a bifunctional chelating compound of the present invention with a protein to form a chelating compound-protein conjugate, then reacting the conjugate with a radionuclide metal to form a complex of the radionuclide metal at the first site of the chelating compound, and incubating the resulting conjugate-radionuclide metal complex at a temperature of 37° C. or less to promote the transfer of the radionuclide metal to the second site, thereby forming a protein-bound chelate of the radionuclide metal. An alternative method for radiolabeling a protein comprises the steps of reacting a chelating compound of the present invention with a radionuclide metal to form a complex of the radionuclide metal at the first site, incubating the complex to promote transfer of the radionuclide metal to the second site, thereby forming a chelate, then reacting the compound with the protein, thereby producing a chelate-protein conjugate.

Conjugates comprising a protein having a chelating compound (or a radiolabeled chelate) of the invention bound thereto also are disclosed. The radionuclide metal is selected from, for example, $^{99m}Tc$, $^{188}Re$, $^{186}Re$, $^{67}Cu$, $^{64}Cu$, $^{212}Pb$, $^{212}Bi$, and $^{109}Pd$. The protein may be an antibody, monoclonal antibody, or fragment thereof, such as a monoclonal antibody specific for cancer cells.

The present invention also provides a method of preparing a chelate of a radionuclide metal comprising reacting the radionuclide metal with the chelating compound described above to form a complex at the first site, then incubating the complex at a temperature of 37° C. or less to promote the transfer of the radionuclide metal to the second site, thereby forming the chelate.

DETAILED DESCRIPTION OF THE INVENTION

Figure 1A:
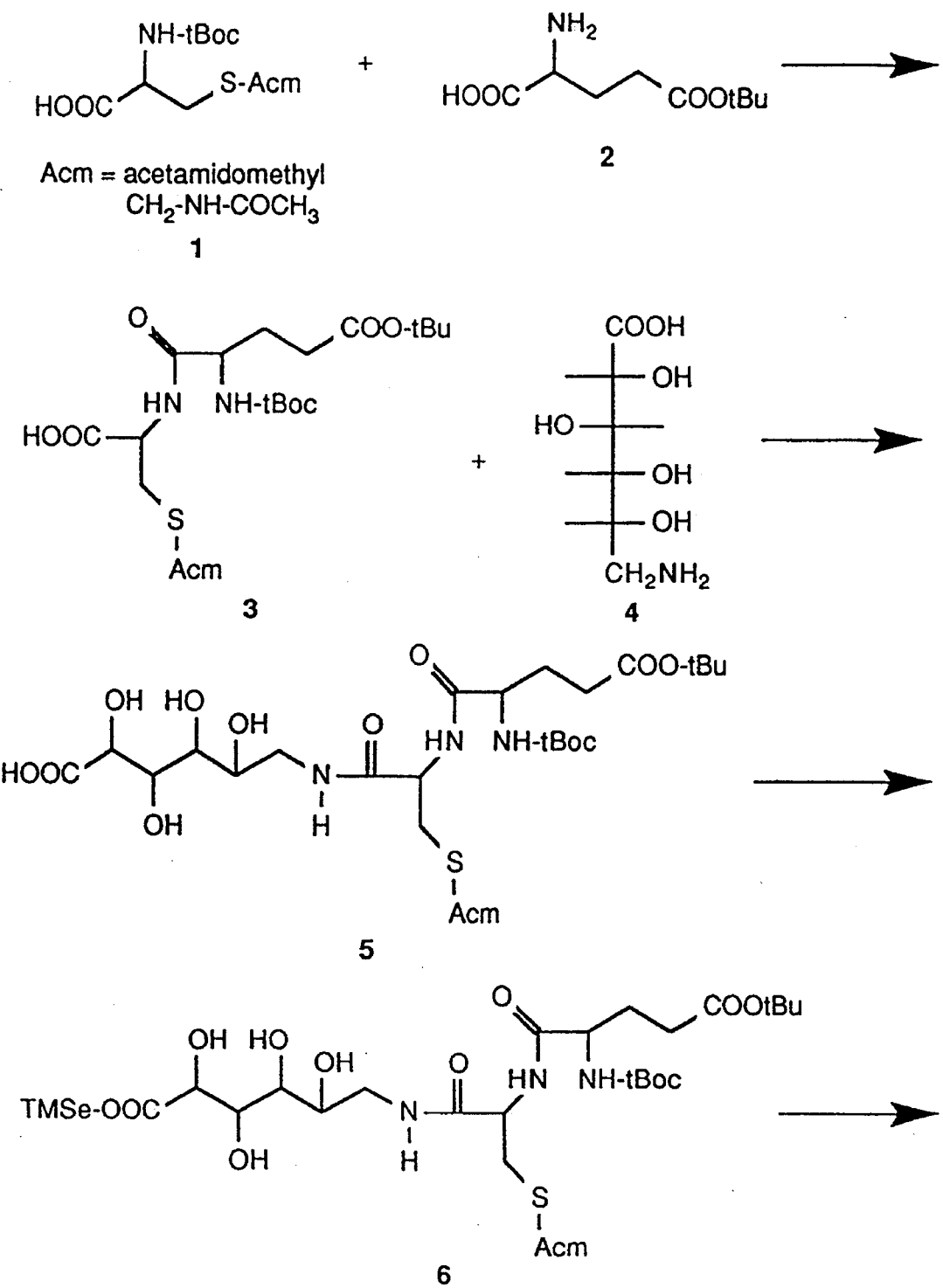
FIGS. 1a and 1b illustrate the pathway for the synthesis of a bifunctional diamidodimercapto anchimeric chelate.

The novel compositions of the present invention are radiometal chelates useful for both diagnostic and therapeutic treatment. The chelating compounds have a first site capable of rapidly forming a labile complex with a radionuclide metal and a second site capable of forming a stable coordinate covalent chelate with a radionuclide metal. The radionuclide metal complex that forms at the first site has a faster rate of formation but a lower thermodynamic stability than the radionuclide metal chelate that forms at the second site. When a radionuclide metal is combined with the compound, a complex rapidly forms at the first site and the radiometal is thereafter transferred to the second site, thereby forming a thermodynamically stable radiometal-chelate complex. In some situations the chelating compound having first formed a complex with a radionuclide metal must be heated in order to transfer the radionuclide metal to the second site. Heating of the compound to about 37° C. or less generally is sufficient to transfer the radiometal from the labile first site to the thermodynamically stable second site. The temperature required to promote transfer of the metal from the first site to the second site will depend on such factors as the exact chemical structure of the chelating compound, as discussed more fully below. One advantage of compounds of the instant invention is that they rapidly form thermodynamically stable complexes with radiometals without the necessity of heating above physiological temperatures. It is believed that these compounds exhibit this unusual property because of the neighboring group effect. Compounds exhibiting this effect have neighboring functional groups that participate in the overall reaction and exhibit more rapid kinetics than compounds without reactive neighboring functional groups.

The compounds of the instant invention can be viewed as molecules having both a weak complexing site (Site 1) and a strong chelating site (Site 2) covalently linked together. It is believed that when this compound is mixed with a metal M, a relatively labile complex rapidly forms according to Equation (1) below.

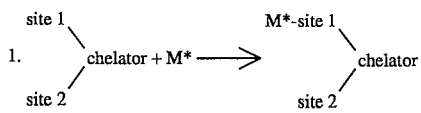

Subsequently, when sufficient heat is applied (or when incubated at room temperature in some cases), the weak complexing moiety of the molecule releases the metal to the strong chelating moiety, resulting in rearrangement of the complex according to Equation (2) below.

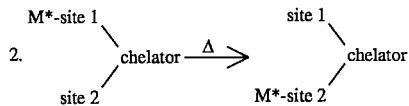

It is unlikely that the metal is actually released into solution during the rearrangement represented by Equation (2); rather the rearrangement is likely to occur with anchimeric assistance. (See W. Page, *Chem. Soc. Rev.*, 2, 295–323 (1973); and J. March, *Advanced Organic Chemistry*, McGraw-Hill, New York, 2d edition, p. 280, for discussions of anchimeric assistance.)

The functional groups present at the first site (Site 1) forming the weak complex are generally groups comprising two or more atoms selected from oxygen, nitrogen, or phosphorous (in the form of oxides such as phosphate or phosphonate). Preferred functional groups present at the first site comprise hydroxyl groups or amino groups, either alone or in conjunction with carboxyl groups. The portion of the compounds of the invention which functions as the first site may be selected from, for example, iminodiacetate, alkyl phosphonate, alkyl diphosphonate, N-glycine, aminoalkylpolyacetate, alkylhydroxycarboxylate, polyhydroxyaminoalkanes, alkylaminohydroxycarboxylate, and alkyldihydroxydicarboxylate. Preferred substituents Q include substituents selected from the group consisting of polyhydroxycarboxylates, gluconate, tartrate, alkyl phosphonate, alkyl diphosphonate, gluconamide, N-glycine, N-3-aminopropanoate, α-hydroxy acids, α-hydroxy-β-amino acids (e.g., α-hydroxy-β-amino propanoate), α-hydroxy-α-amino acids, deoxyamino uronic acids (e.g., 6-amino-6-deoxy-D-gluconic acid), β-diketones or their enol equivalents,

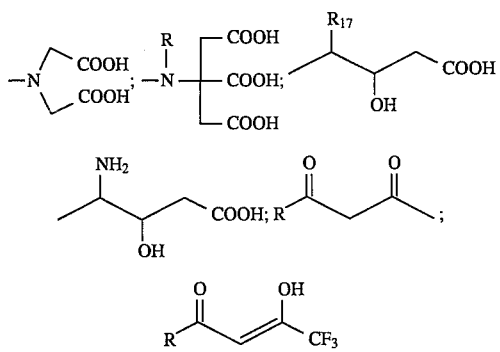

wherein R is $C_1$-$C_5$ lower alkyl and $R_{17}$ is selected from hydrogen, lower alkyl, or $R_{15}$—Z, wherein $R_{15}$ represents a divalent spacer and Z represents a group reactive with a protein, as described below under Formula I. Other compounds having suitable functional groups to form the initial complex at the first site include derivatives of the above groups.

The chelating compounds of the instant invention generally contain, at the second site, a heteroatom chain containing at least four donor atoms chosen from sulfur, nitrogen, and oxygen. These donor atoms are capable of forming coordinate covalent bonds with a radionuclide metal so that a thermodynamically stable radionuclide metal-chelate forms at the second site. It is preferred that the donor atoms include at least one divalent sulfur atom and at least two nitrogen atoms and that the sulfur atom is positioned at one terminus of the heteroatom chain. In addition to the heteroatoms, the heteroatom chain contains from 6 to 7 carbon atoms positioned such that at least two of the carbon atoms are interposed between any two of the donor atoms. In one embodiment of the invention, the donor atoms in the heteroatom chain are two nitrogen atoms and two sulfur atoms. Chelating compounds of this type are referred to hereinafter as $N_2S_2$ compounds. The sulfur atoms in this compound are generally divalent sulfur and the nitrogen atoms are independently either amide or amine nitrogen. In an alternative embodiment of the instant invention, the donor atoms in the heteroatom chain of the second site consist of three nitrogen atoms and one sulfur atom. Compounds of this type are referred to hereafter as $N_3S$ compounds in which the sulfur atom is divalent sulfur and the nitrogen atoms are independently amide or amine nitrogen.

The second site of the chelating compound is the strong chelating moiety of the molecule. Exemplary compounds forming strong coordinate covalent chelates with radionuclide metals which may be used as the strong chelating moiety are $N_2S_2$ compounds such as the bis(mercaptoalkanoamido)alkanoic acids. Examples of these are 2,3-dimercaptoacetamidobutanoate, and 4,5-dimercaptoacetamidopentanoate, generally referred to as $CO_2$-DADS compounds, as well as 1,2-dithioacetamidoethane (DADS), 4,5-dithioacetamidopentanoic acid, and amino-amides such as 4-thioacetamido-5-thioethylaminopentanoic acid. These compounds can be synthesized by procedures described in Fritzberg U.S. Pat. No. 4,444,690, herein incorporated by reference, European Patent Application Publication No. 188, 256, and copending U.S. patent application Ser. No. 065, 017, filed Jun. 19, 1987 now U.S. Pat. No. 5,175,343. Exemplary $N_3S$ compounds that form strong coordinate covalent chelates with radionuclide metals are mercaptoacetylglycylglycylglycine ($MAG_3$) compounds synthesized by procedures described in Fritzberg et al., *J. Nucl. Med.* 27:111–116 (1986), herein incorporated by reference, and European Patent Application Publication No. 173,424. Suitable MAG$_3$ compounds include not only MAG$_3$ per se, but also analogous compounds in which the terminal glycine is replaced by a β, γ, or δ amino acid, for example mercaptoacetylglycylglycyl-γ-aminobutyrate.

It is preferred that each terminal sulfur atom in the heteroatom chain of the second site be conjugated with a protective group. The sulfur-protective groups may be varied widely, being acyl groups, thio groups or other compounds which provide protection of the thio group during subsequent manipulations. The sulfur-protective groups also serve to stabilize the chelating compounds by preventing reaction of the sulfurs with groups that are part of the chelating compound itself. For example, if the protecting groups are replaced with hydrogens, the sulfurs may displace an active ester protein conjugation group from the chelating compound.

Illustrative sulfur-protective groups include benzoyl, acetyl, acetamidomethyl, m- or p-phthaloyl, thioglycolic, o-carboxythiophenol, ethylthiocarbonate, β-mercaptopropionic, tetrahydropyranyl, ethoxyethyl, sulfonato, acetamidomethyl, etc. Alternatively, cyclic di- or polysulfides may be formed. Disulfides may be prepared using sulfinyl halides, dinitrothiophenoxide-substituted mercaptans, with mild oxidation in the presence of excess of the protective group, etc.

The protective groups may be removed in a variety of ways. Thioesters may be hydrolyzed using aqueous ammonia, sodium alkoxide in alkanol, or any conventional technique. Disulfides may be cleaved with dithiothreitol, glutathione, β-mercaptoethylamine, or other conventional reagent. Cleavage of the disulfide may occur prior to or after conjugation to the polypeptide.

In one embodiment of the invention, the sulfur-protecting group, when taken together with the sulfur atom(s) to be protected, represents a thioacetal or hemithioacetal. These sulfur-protective groups are displaced during the radiolabeling reaction, conducted at acidic pH, in what is believed to be metal-assisted acid cleavage; and covalent bonds form between the sulfur atoms and the radionuclide metal. Advantages of these sulfur-protective groups include the fact that a separate step for removal of the sulfur-protective groups is not necessary. The radiolabeling procedure thus is simplified, which is especially advantageous when the chelating compounds are to be radiolabeled in a hospital laboratory shortly before use. In addition, the basic pH conditions and harsh conditions associated with certain known radiolabeling procedures or procedures for removal of other sulfur-protective groups are avoided. Thus, base-sensitive groups on the chelating compound survive the radiolabeling step intact. Such base-labile groups include any group which may be destroyed, hydrolyzed, or otherwise adversely affected by exposure to basic pH. In general, such groups include esters, Michael-type acceptors (e.g., maleimides) and isothiocyanates, among others. The use of thioacetal or hemithioacetal protective groups, therefore, is especially advantageous when the chelating compound is radiolabeled prior to conjugation of the resulting chelate to a protein (the "pre-formed" approach, described below), since base-labile protein conjugation groups survive the radiolabeling procedure. Another advantage is that these protective groups (especially the hemithioacetals) are relatively easily displaced from the compound, so that the chelating compounds of the invention may be radiolabeled under physiologically acceptable conditions of pH and temperature.

Thioacetals and hemithioacetals which may be used in the present invention include those groups which effectively maintain the sulfurs in a nonreactive state until the radiolabeling step, at which time the protective groups are displaced in the presence of the metallic radioisotope under acidic conditions. In general, the hemithioacetal S-protecting groups are somewhat more acid labile in the radiolabeling reaction than the thioacetal groups, and therefore are generally preferred.

When hemithioacetal protective groups are used, each sulfur atom to be protected has a separate protective group attached to it, which, together with the sulfur atom, defines a hemithioacetal group. Preferred hemithioacetals generally are of the following formula, wherein the sulfur atom is a sulfur atom of the chelating compound, and a separate protecting group is attached to each of the sulfur atoms on the chelating compound:

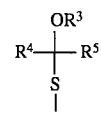

wherein R$^3$ is a lower alkyl group, preferably of from two to five carbon atoms, and R$^4$ is a lower alkyl group, preferably of from one to three carbon atoms. Alternatively, R$^3$ and R$^4$ may be taken together with the carbon atom and the oxygen atom shown in the formula to define a nonaromatic ring, preferably comprising from three to seven carbon atoms in addition to the carbon and oxygen atoms shown in the formula. R$^5$ represents hydrogen or a lower alkyl group, wherein the alkyl group preferably is of from one to three carbon atoms. Examples of such preferred hemithioacetals include, but are not limited to:

Tetrahydrofuranyl

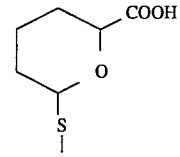

6-carboxy tetrahydropyranyl

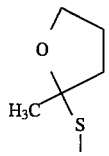

2-methyl tetrahydrofuranyl

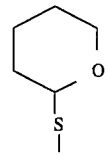

Tetrahydropyranyl

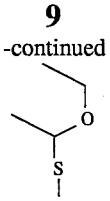

ethoxyethyl

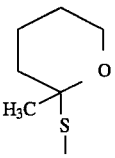

2-methyl tetrahydropyranyl

When the chelating compound comprises two or more sulfur donor atoms, the sulfur-protective groups may be the same or different. In some cases, the compounds may be synthesized more easily when a different protective group is attached to each sulfur donor atom. For example, a chelating compound having two sulfur donor atoms may contain one hemithioacetal sulfur-protecting group and one acetamidomethyl surfur protecting group.

The chelating compound of the instant invention also contains a flexible divalent linker which connects the labile complexing first site to the thermodynamically stable chelating second site. It is preferred that the flexible linker comprise from about two to about six methylene groups or equivalents comprising covalent σ-bonds and may contain one or more of the following: ether, thioether, amine or amide groups. Methylene chains or equivalents of this length are of suitable length and flexibility to allow transfer of a radionuclide metal from the first site to the second site via first-order kinetics characteristic of compounds exhibiting the nearest neighbor effect.

The chelating compounds of the present invention can be synthesized by covalently linking compounds which form strong coordinate covalent chelates with radionuclide metals to compounds known to rapidly form labile complexes with radionuclide metals. Covalent linking of the compounds through the flexible divalent linker can be achieved by conventional procedures which will vary according to the chemical structure of the compounds. For example, 2,3-dimercaptoacetamidopropanoate, having the terminal sulfurs protected with either ethoxyethyl or acetamidomethyl, can be reacted with N-hydroxysuccinimide and N,N'-dicyclohexylcarbodiimide. The resulting active ester can then be reacted with 6-amino-6-deoxy-D-gluconic acid to produce 2,3-di(S-ethoxyethylmercaptoacetamido)-propanoyl-6-amino-6-deoxy-D-gluconic acid. Other exemplary monofunctional (as opposed to bifunctional) anchimeric chelating compounds produced analogously include 4,5-di(S-ethoxyethylmercaptoacetamido)pentanoyl-6-amino-6-deoxy-D-gluconic acid and 3,4-di(S-ethoxyethylmercaptoacetamido)butanoyl-6-amino-6-deoxy-D-gluconic acid.

Compounds of this type are particularly useful for replacing radionuclide metal-chelate systems that form highly stable complexes but with slow kinetics. These are exemplified by certain Tc and Re diamido dimercapto complexes in which disulfide formation, oxidation, etc., and cluster formation (i.e., one metal atom associated with more than one chelating compound) restricts the chelation kinetics to relatively slow rates. However, once formed, such complexes are particularly stable. Such complexes have found practical use as bifunctional chelates for labeling proteins (antibodies). Due to the slow kinetics of chelation, commercial application has been limited to the pre-formed chelate approach (described below) (see copending U.S. patent application Ser. No. 065,017, filed Jun. 19, 1987, now U.S. Pat. No. 5,175,343 entitled "Metal Radionuclide Labeled Proteins for Diagnosis and Therapy"), in which the slowness can be overcome by heating at the small molecule stage (e.g., at temperatures of about 75° C.) to form the radiolabeled chelate, and then conjugating the chelate to the protein at room temperature. This approach is much more complex than a post-form approach (described below) in which the metal specifically forms a $N_2S_2$ type chelate in a chelating compound already conjugated to the antibody. Successful application that avoids nonspecific, uncontrolled binding of Tc and Re to the protein provides a much simpler labeling and, hence, product formulation. The use of the rapid complex formation at the first site to bring the metal into position to accelerate $N_2S_2$ chelation provides a means to achieve more rapid chelation of the metal radionuclide than association with nonspecific binding sites on the antibody.

Compounds of the instant type are particularly useful for chelating radionuclide metals having diagnostic or therapeutic use. These radiometals include, but are not limited to, $^{99m}Tc$, $^{188}Re$, $^{186}Re$, $^{67}Cu$, $^{64}Cu$, $^{212}Pb$, $^{212}Bi$, $^{105}Rd$, $^{97}Ru$, and $^{109}Pd$. Methods for preparing these isotopes are known. Molybdenum/technetium generators for producing $^{99m}Tc$ are commercially available. Procedures for producing $^{186}Re$ include the procedures described by Deutsch et al., *Nucl. Med. Biol.*, 13:4:465–477, (1986) and Vanderheyden et al., *Inorganic Chemistry*, 24:1666–1673, (1985), and methods for production of $^{188}Re$ have been described by Blachot et el., *Intl. J. of Applied Radiation and Isotopes*, 20:467–470, (1969) and by Klofutar et el., *J. of Radioanalytical Chem.*, 5:3–10, (1970). Production of $^{109}Pd$ is described in Fawwaz et el., *J. Nucl. Med.*, 25:796 (1984). Production of $^{212}Pb$ and $^{212}Bi$ is described in Gansow et al., *Amer. Chem. Soc. Symp. Ser.*, 241:215–217 (1984), and Kozah et el., *Proc. Nat'l. Aced. Sci. USA*, 83:474–478 (1986).

The method for preparing a radionuclide metal-chelate, according to the present invention, comprises reacting a radionuclide metal of the type described above with the instant chelating compound to form a complex at the first site, essentially as depicted in Equation (1) above. The conditions suitable for carrying out this reaction are known to those skilled in the art and depend both on the type of radiometal to be chelated and its normal valence. For example, to prepare the technetium chelate, the chelating compounds of the instant invention may be combined with a pertechnetate solution in the presence of a reducing agent (e.g., stannous ion or dithionite under conventional conditions), whereby the technetium complex is formed at the first site as a stable salt. The corresponding rhenium complex may be formed by reducing perrhenate with stannous ion or dithionite. Site 1 complexes of $^{212}Pb$, $^{212}Bi$ and $^{109}Pd$ may be prepared by simply combining the appropriate salt of the radionuclide metal with the chelating compound. It is not necessary to treat the lead, bismuth, palladium, and copper isotopes with a reducing agent prior to complexation because such isotopes are already in an oxidation state suitable for complexation (see for example, Fritzberg et al., (1986)). After the initial complex has formed, it is incubated at mild temperatures to promote transfer of the radionuclide metal to the second site, thereby forming a thermodynamically stable chelate, essentially as depicted in Equation (2) above. The preferred compounds of the instant invention are those that require heating to 37° C. or less to effect the transfer of the radiometal from the first site to the second site.

The temperature required to promote the transfer of the radionuclide metal from the first site to the second site will vary according to such factors as the exact chemical structure of the chelating compound. For example, certain sulfur-protecting groups are displaced at lower temperatures during radiolabeling than are others. Also, slightly higher temperatures may be required to promote transfer of the radiometal when the chelating compound comprises one or more amide groups (i.e., a carboxyl group adjacent to a nitrogen donor atom, as shown below). For some chelating compounds of the present invention, incubation at room temperature is expected to be sufficient to promote transfer of the radionuclide metal to the second site, which binds the radionuclide metal in the form of a strong, stable chelate. In general, the radiolabeling reaction mixture is not cooled, but is incubated at a temperature between ambient temperature and about 37° C. for a length of time sufficient to promote transfer of the metal to the second site, thus forming the chelate.

Optionally, a chelating compound of the instant invention additionally comprises a conjugation group that is capable of reacting with a protein thereby binding the chelating compound to the protein. Chelating compounds of this type are hereinafter referred to as bifunctional chelating compounds. The conjugation group is generally attached through a spacer group to any carbon or nitrogen atom of the chelating compound. A variety of functional groups suitable for conjugation to a protein in an aqueous reaction medium under conditions that preserve the biological activity of the protein may be employed. Among the suitable conjugation groups are those selected from the group consisting of esters, active esters, halomethyl ketones, maleimide groups, other Michael-type acceptors, free amines, and isothiocyanate groups. Proteins contain a variety of functional groups (e.g., carboxylic acid or free amine groups) which are available for reaction with the protein conjugation group on the chelating compound. One or another of the groups may be preferred, depending upon the particular radionuclide metal, the protein, the chelating compound, and the conditions for conjugation. As used herein, the term "aqueous medium" is meant to include not only totally aqueous media but also mixed aqueous/organic media, wherein the organic component is present only in a relatively low concentration; i.e., a concentration low enough to minimize damage to polypeptides (e.g., denaturation).

A variety of esters may be used as the protein conjugation group, including aromatic esters containing electron-withdrawing groups, or α-substituted methyl esters (in which the substituents are electron-withdrawing groups, such as, but not limited to, —CH$_2$CN, —CH$_2$—CO—CH$_2$CH$_3$ or CH$_2$—CO—CH$_3$).

Preferred esters for use in the present invention have several structural features that impart the desired stability and reactivity to the esters. For example, preferred esters should be relatively stable, especially with respect to hydrolysis in aqueous solutions. Chelating compounds comprising such esters may be added to aqueous reaction mixtures or mixed aqueous/organic reaction mixtures (i.e., for radiolabeling or for protein conjugation reactions) with relatively little hydrolysis of the ester group. Thus, such hydrolysis-resistant esters are particularly useful in reactions with proteins, since such reactions preferably are conducted under aqueous conditions to prevent denaturation of the proteins that may occur in organic solvents. Advantageously, the ester is sufficiently stable to allow preparation of the chelating compound ahead of time and storage, even under humid conditions, until needed, with the ester group remaining substantially intact.

The term "active ester" is known to refer to esters that are highly reactive in nucleophilic substitution reactions. Preferred active esters for use in the present invention are highly reactive toward groups on polypeptides so that the active ester-containing chelate compounds are bound to the polypeptides through the reaction. Reaction of an ester with a free amine group (present on lysine residues) on a protein produces an amide bond. These active esters comprise leaving groups (i.e., the —OR' portion of an ester R—CO—OR') that are sufficiently electron-withdrawing to increase the susceptibility of the carbonyl to attack by nucleophilic groups on the protein. The kinetics of the reaction preferably are such that the ester reacts quickly with nucleophilic groups on the polypeptide. Thus, the free unreacted ester groups, potentially susceptible to hydrolysis (especially if the reaction is conducted at a basic pH), are subjected to the aqueous reaction conditions for only a short time. Hydrolysis of the ester, therefore, is further minimized, and a relatively high ratio of the desired reaction to hydrolysis of the ester results.

Common esters that find use are the o- and p-nitrophenyl, 2-chloro-4-nitrophenyl, cyanomethyl, 2-mercaptopyridyl, hydroxybenztriazole, N-hydroxysuccinimide, trichlorophenyl, tetrafluorophenyl, 2-fluorophenyl, 4-fluorophenyl, 2,4-difluorophenyl, o-nitro-p-sulfophenyl, N-hydroxyphthalimide, N,N-diethylamino, N-hydroxypyrrolidone, tetrafluorothiophenyl, and equivalents. For the most part, the esters will be activated phenols, particularly nitro-activated phenols and cyclic compounds based on hydroxylamine. As other hydroxylic compounds become available, these also may find use in this invention.

Especially good results are achieved by using a 2,3,5,6-tetrafluorophenyl ester, which is an active ester having the above-described properties of stability and high reactivity. Another ester group exhibiting high reactivity toward proteins is a thiophenyl ester.

The use of esters comprising nitro groups may be disadvantageous in certain circumstances. For example, the nitro group may be reduced by stannous ion that may be present when the stannous ion is added as a pertechnetate or perrhenate reducing agent, as described above.

Alternatively, the protein and/or chelating compound may be derivatized to expose or attach additional reactive functional groups. The derivatization may involve attachment of any of a number of linker molecules such as those available from Pierce Chemical Company, Rockford, Ill. (See the Pierce 1986–87 General Catalog, pages 313–354.) Alternatively, derivatization may involve chemical treatment of the protein, e.g., glycol cleavage of the sugar moiety of a glycoprotein antibody with periodate to generate free aldehyde groups. The free aldehyde groups on the antibody may be reacted with free amine or hydrazine groups on the chelating compound to bind the agent thereto. (See U.S. Pat. No. 4,671,958.) Procedures for generation of free sulfhydryl groups on antibodies or antibody fragments also are known. The sulfhydryl groups are reactive with maleimide and amino groups. (See U.S. Pat. No. 4,659,839.)

The protein to which the chelating compound is to be attached may be varied widely, depending upon the nature of the use of the radionuclide metal. In general, the protein delivers the chelated radionuclide to a desired target site in vivo. Suitable proteins include, but are not limited to, receptors, hormones, lymphokines, growth factors, substrates, and particularly compounds binding to surface membrane receptors, where the complex may remain bound to the surface or become endocytosed. Among receptors are surface membrane receptors, antibodies (including monoclonal antibodies) enzymes, naturally occurring receptors, lectins, and the like. Of particular interest are immunoglobulins or their equivalent, which may be whole antibodies or fragments thereof, e.g., Fab, Fab', F(ab')$_2$, or F$_v$ fragments, or T-cell receptors, etc. As used herein, the term "protein" includes polypeptides, proteins, or fragments thereof. These proteins and polypeptides may be modified, provided the biological activity necessary for the intended diagnostic or therapeutic application of the radiolabeled polypeptide is retained. For example, a modified antibody or fragment thereof may be used as long as binding to the desired antigen still occurs. The amino acid sequence of a protein may be varied (e.g., by known mutation techniques or deletion of portions thereof) as long as the desired biological activity (e.g., binding of the protein to specific target cells, tissues, or organs) is retained. Methods of modifying proteins also may include, among others, attachment of bifunctional linker compounds that react with both a group on a protein and with the Z group on the chelating compounds, thereby binding the chelating compound to the protein through the linking compound. The protein may be purified from a natural source or may be synthetic (e.g., produced by recombinant DNA technology or chemical synthesis procedures).

Proteins that bind to the desired target site are said to be "target specific." For example, antibodies that bind to a particular antigen are said to be target specific for that antigen. It is to be understood that such proteins or antibodies are rarely 100% specific for a target site, and a certain degree of cross-reactivity with other tissues is common. An example of a target site is a cancer cell. Many antigens associated with various types of cancer cells have been identified, and monoclonal antibodies specific for a number of these cancer cell-associated antigens also are known. Among the many such monoclonal antibodies which may be used are anti-TAC, or other interleukin 2 receptor antibodies; 9.2.27 and NR-ML-05 to the 250 kilodalton human melanoma-associated proteoglycan; NR-LU-10 to 37–40 kilodalton pancarcinoma glycoprotein; NR-CO-02 to carcinoembryonic antigen (CEA) and colon carcinoma; NR-CE-01 to CEA; and OVB$_3$ to an as yet unidentified cancer-associated antigen. Antibodies derived through genetic engineering or protein engineering may be employed as well. Such antibodies are examples of the many target specific proteins suitable for use in accordance with the present invention.

An example of a chelating compound of the present invention is represented by structural Formula I.

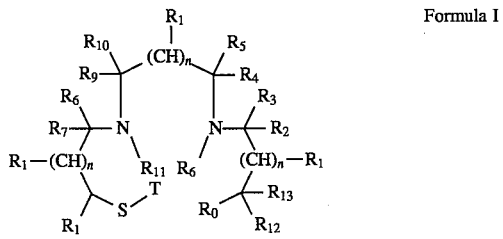

Formula I

1) Wherein:
 a) T is a sulfur-protecting group;
 b) $R_0$ is S—T, carboxylic oxygen or

;

c) the R groups designated $R_1$ through $R_{11}$ are independently selected from COOH, $R_{14}$ and $R_{15}$—Z, wherein any two of said R groups, when bonded to the same carbon atom, may be taken together to form an oxo group, with the provisos that:
 i) $R_7$ and $R_8$ taken together, and $R_9$ and $R_{10}$ taken together, are not both simultaneously oxo;
 ii) $R_2$ and $R_3$ taken together, and $R_4$ and $R_5$ taken together, are not both simultaneously oxo;
 iii) $R_4$, $R_5$, $R_9$, and $R_{10}$ may all be taken together to form a hydrocarbon ring;
 iv) $R_6$ is hydrogen when either $R_2$ and $R_3$ or $R_4$ and $R_5$ represent an oxo group;
 v) $R_{11}$ is hydrogen when either $R_7$ and $R_8$ or $R_9$ and $R_{10}$ represent an oxo group;
 vi) each of $R_7$, $R_8$, $R_9$, and $R_{10}$ are hydrogen when $R_{11}$ is $R_{15}$—Z or $R_{16}$;
 vii) each of $R_2$, $R_3$, $R_4$, and $R_5$ are hydrogen when $R_6$ is $R_{15}$—Z or $R_{16}$;
 viii) $R_6$ and $R_{11}$ cannot be COOH;
 d) $R_{12}$ and $R_{13}$ are (1) independently $R_{14}$ or $R_{15}$—Z when $R_0$ is either S—T or

or (2) taken together to form oxo when $R_0$ is either carboxylic oxygen or

, with the proviso that when $R_{12}$ and $R_{13}$ are oxo and $R_0$ is

and one of these two $R_1$ groups is $R_{15}$—Z or $R_{16}$, the other $R_1$ group is hydrogen;
 e) $R_{14}$ is hydrogen, lower alkyl, or $R_{16}$;
 f) n is 0 or 1 provided that n equals 1 not more than once;
 g) $R_{15}$ is a divalent spacer selected from substituted or unsubstituted lower alkyl, which may additionally comprise one or more groups selected from —O—, —NH—, —NR—, —CO—, —CO$_2$—, —CONH—, —S—, —SO—, —SO$_2$—, —CO$_2$NH—, and —SO$_2$NR—, where R is selected from C$_1$-C$_3$ alkyl;
 h) Z is a functional group suitable for reacting with a protein, protein fragment, or polypeptide under conditions that preserve biological activity of the protein, protein fragment, or polypeptide;
2) wherein said compound comprises at least one substituent $R_{15}$—Z; and
3) wherein at least one of the groups $R_1$-$R_{14}$ is substituent $R_{16}$ having the formula:

wherein:
 a) one or more $R_{17}$ groups are bonded to any carbon or nitrogen atom and are selected from the group hydrogen, lower alkyl, or $R_{15}$—Z;
 b) X is a radical selected from the group consisting of fully substituted carbon, nitrogen, oxygen, sp$^2$ or sp carbon, or amide or imide nitrogen;

c) p in an integer, 2, 3, 4, 5, or 6 provided that:
   i) when p is 2 or 3, X is fully substituted carbon;
   ii) when p is 4, X is fully substituted carbon, nitrogen, or oxygen, further provided that at least three radicals X are fully substituted carbon;
   iii) when p is 5 or 6, at least three radicals X are fully substituted carbon and further provided that only one radical X may be $sp^2$ or sp carbon, amide or imide nitrogen; and
d) Q represents the first site.

In compounds of the type represented by Formula I, Q may be selected from among the compounds and structures described above as being suitable for use as the first site, i.e., the weak complexing moiety of the chelating compound of the invention. The substituent $R_{15}$—Z is present when the chelating compound is to be attached to a protein. The Z group may be chosen from the protein conjugation groups described above.

The chelating compounds represented by Formula I comprise, at the second site, a heteroatom chain containing four donor atoms chosen from sulfur, oxygen, and nitrogen. Two of the donor atoms are nitrogen, independently either amino or amido. One of the donor atoms positioned at one end of the heteroatom chain is sulfur, and the other donor atom, located at the other end of the heteroatom chain, is either carboxylic oxygen, sulfur, or amino nitrogen. Accordingly, the compounds represented by Formula I are referred to by their donor atom composition at the second site; namely, $N_2SO$, $N_2S_2$, and $N_3S$, respectively.

In addition to the donor atoms, there are 6 or 7 carbon atoms in the heteroatom chain that comprises the second site. The carbon atoms are positioned so that at least two carbons interpose between any two donor atoms of the heteroatom chain. When two carbon atoms are positioned between two donor atoms, they, together with a radionuclide metal, define a 5-member ring in a portion of the heteroatom chain. Five-member rings are preferred at the second site because this planer structure allows formation of the most stable chelate with a radionuclide metal. Accordingly, the most preferred chelate compound represented by Formula is produced when n equals zero in each case or the heteroatom chain comprises a total of 6 carbon atoms. This embodiment produces a particularly stable chelating compound in which the heteroatom chain, together with the radionuclide metal, defines three 5-membered rings.

Suitable chelating compounds are obtained when n equals 1 in Formula I, provided that n equals 1 only once or the heteroatom chain comprises a total of 7 carbon atoms. In this embodiment, two donor atoms are separated by three carbon atoms that, when taken together with the radionuclide metal, defines a 6-member ring in a portion of the heteroatom chain. Accordingly, when four donor atoms and seven carbon atoms comprise the heteroatom chain of the second site, these atoms, together with the radionuclide metal, define two 5-membered rings and one 6-membered ring. Chelating compounds of the type represented by Formula I, containing more than one 6-member ring at the second site, are generally not suitably stable unless donor atoms at the first site also participate in chelation of the radionuclide metal.

The chelating compounds represented by Formula I have a flexible divalent linking group that links the first site with the second site. This linking group, defined as $(X)_p$ in Formula I, may be from about 2 to 6 methylene equivalents in length and must possess sufficient flexibility to allow intramolecular transfer of a radionuclide metal from the first site to the second site by heating to 37° C. or less. Accordingly, when p in Formula I is 2 or 3, radical X must be fully substituted carbon, nonlimiting examples of which are: —$CH_2$—$CH_2$— and —$CH_2$—$CH_2$—$CH_2$—. The hydrogens of these exemplary compounds may be independently substituted with other groups, provided the carbon atoms remain fully substituted.

When p is 4, X must be fully substituted carbon, nitrogen, or oxygen, provided at least three radicals X are fully substituted carbon. Nonlimiting examples of these are: —$CH_2$—$CH_2$—$CH_2$—$CH_2$—, —$CH_2$—O—$CH_2$—$CH_2$—, and —$CH_2$—$CH_2$—NH—$CH_2$—. Fully substituted oxygen and nitrogen may be located in any position in these exemplary compounds and, as above, the hydrogens may be independently substituted with other groups, provided that radical X remains fully substituted.

When p is 5 or 6, at least 3 radicals X must be fully substituted carbon. The other radicals may be fully substituted carbon, nitrogen, or oxygen, and one of the other radicals may be $sp^2$ or sp carbon, amide or imide nitrogen. Nonlimiting examples of these are: —$CH_2$—$CH_2$—$CH_2$—$CH_2$—$CH_2$—, —$CH_2$—$CH_2$—$CH_2$—$CH_2$—$CH_2CH_2$—, —$CH_2$—NH—$CH_2$—$CH_2$—$CH_2$—, $CH_2$—$CH_2$—NH—CO—$CH_2$—$CH_2$—, —$CH_2$—NH—NH—CO—$CH_2$—, and —$CH_2$—O—$CH_2$—NH—CO—$CH_2$—. The carbons, nitrogens, and oxygens may be located at any position in these exemplary compounds and, as above, the hydrogens may be independently substituted with other groups, provided that only one radical X is $sp^2$ or sp carbon, amide or imide nitrogen.

Compounds of the type described above and represented by Formula I can be prepared by procedures described in the examples. One of ordinary skill, upon reading the examples and examining the structure represented by Formula I, will be able to synthesize the plurality of compounds represented by Formula I by substituting appropriate reagents in the reaction schemes provided.

Examples of bifunctional compounds of the instant invention suitable for conjugation to a protein comprise those compounds represented by Formulae II–XIV.

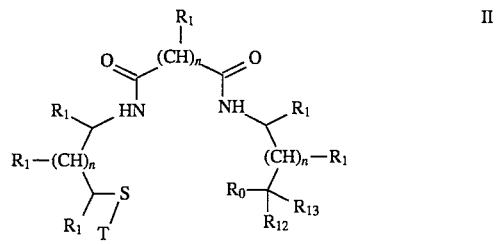

II

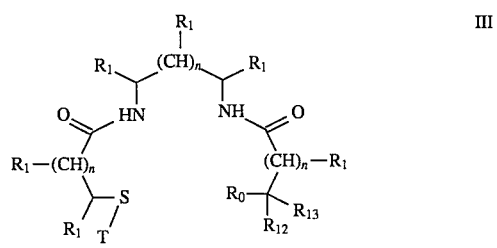

III

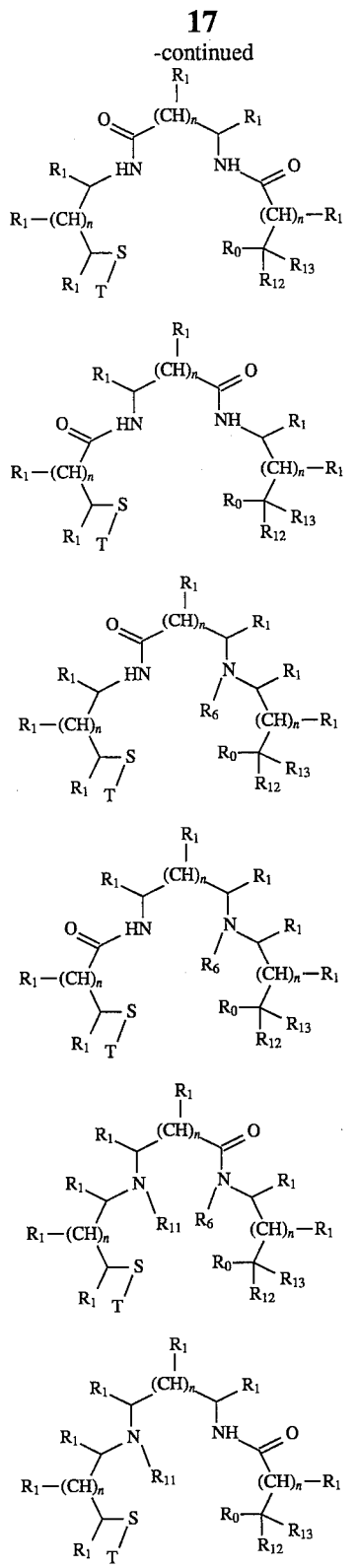
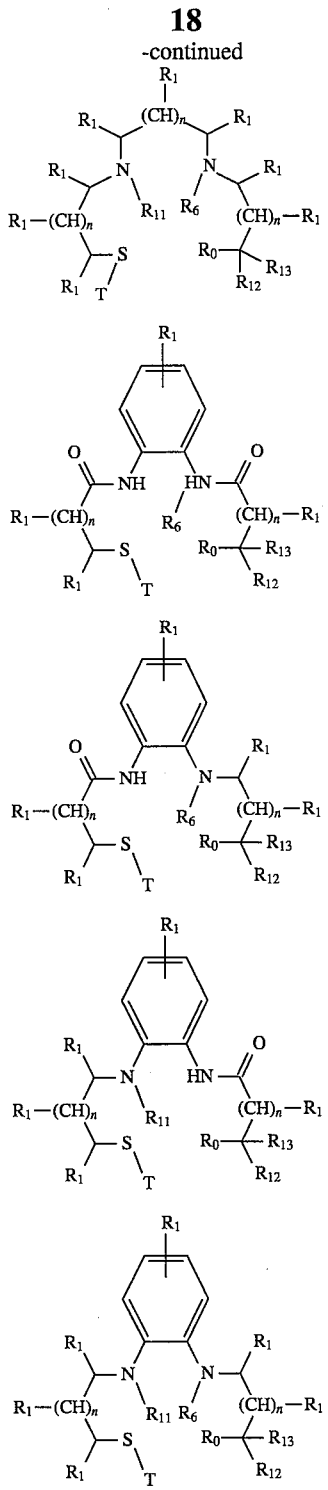
Wherein the symbols T, $R_0$, $R_1$, $R_6$, $R_{11}$, $R_{12}$, $R_{13}$, and n are as described for formula I above, with the proviso that:
(a) each compound comprises at least one substituent $R_{15}$—Z and one substituent $R_{16}$;

(b) when $R_6$ is $R_{16}$ or $R_{15}$—Z, each $R_1$ group attached to a carbon atom adjacent to —N—$R_6$ is hydrogen;

(c) when $R_{11}$ Is $R_{16}$ or $R_{15}$—Z, each $R_1$ group attached to a carbon atom adjacent to —N—$R_{11}$ is hydrogen.

Compounds of the type represented by Formulae II–IV include diamidodimercapto chelates, representative examples of which include S-1-ethoxyethylmercaptoacetyl-γ-(2,3,5,6,-tetrafluorophenoxy)-L-glutamyl-α-S-acetamidomethyl-L-cysteinyl-6-amino-6-deoxy-D-gluconic acid. Compounds of the type represented by Formulae VI–IX include-monoamino monoamido mercaptides, representative examples of which include 4-N-(S-1-ethoxyethylmercaptoacetyl)-5-N'-(isothiocyanatophenethyl)-N'-β-(S-1-ethoxyethyl)mercaptoethyl-diaminopentanoyl-6'-amino-6'-deoxy-D-gluconic acid. Compounds of the type represented by Formula X include diamino mercaptides, representative examples of which include 4-N-methyl-N-β-(S-1-ethoxyethyl)mercaptoethyl-5-N'-(p-isothiocyanatophenethyl)-N'-β-(S-1-ethoxyethyl)mercaptoethyl-diaminopentanoyl-6'-amino-6'-deoxy-D-gluconic acid. Preferred compounds of the type represented by Formulae XI–XIV are $N_2S_2$ chelates containing an aromatic bridge, representative examples of which include 3-(β-1-ethoxyethyl)-acetamido-4-N-(β-1-ethoxyethyl)ethyl-N-(N',N'-dicarboxymethyl)-aminoethyl phenylisothiocyanate. The chemical structure of one preferred compound of the instant invention is represented by Formula XV:

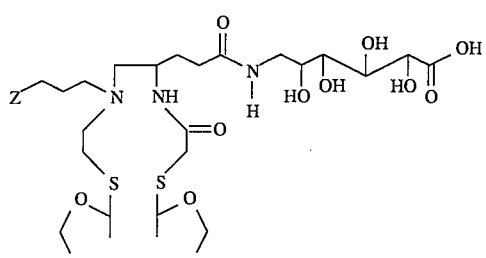

XV wherein Z represents an active ester group or an isothiocyanate group.

Chelating compounds of the type represented by Formulae I–XV are useful for radiolabeling proteins. Generally, two approaches may be employed to radiolabel proteins with the bifunctional chelating agents described herein. The first method is referred to as the post-form approach and is depicted in Equations (3) through (5) below. The method of radiolabeling a protein such as an antibody, according to this approach, consists of first reacting the bifunctional chelating compound with the antibody, thereby forming a chelating compound-antibody conjugate, then admixing the conjugate with the radionuclide metal under conditions suitable for forming a radionuclide metal-chelate-antibody complex in which the radiometal is complexed to the first weak binding site of the chelate. This complex is then incubated at about 37° C. or below, causing intramolecular rearrangement of the complex such that the metal is transferred to the thermodynamically stable second site, thereby producing a stable radionuclide metal-chelate bound to an antibody.

Post-Form Approach

3.
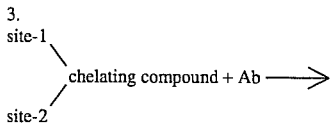

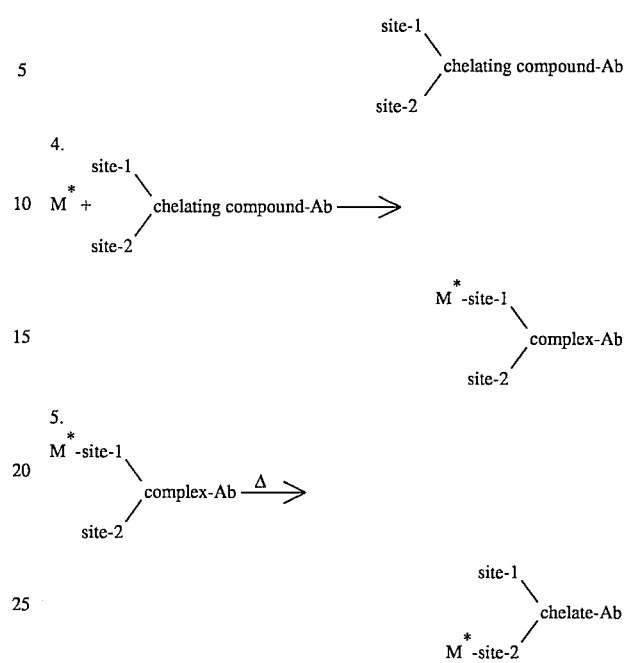

One advantage of employing compounds of the instant invention when used in the post-form approach is that high yields of a thermodynamically stable chelated radionuclide metal can be achieved under conditions that preserve biological activity of the protein. The observation that the stable chelate can be formed at temperatures less than 37° C. greatly enhances the preservation of biological activity of the antibody by avoiding denaturation and aggregation. Prior-art methods for forming thermodynamically stable metal-chelate complexes conjugated to proteins often require the addition of a weak or labile chelating agent to facilitate transfer of the radiometal to the chelate-antibody complex. Even when this strategy is employed, heating to from 50° to 75° C. or more is required to transfer the metal to the chelate antibody complex, resulting in significant loss of biological activity of the antibody.

Another advantage of employing compounds of the instant invention, is that less nonspecific binding of the radionuclide metal to the protein itself occurs. Nonspecific binding is undesirable because the radionuclide metal may attach to a weak radionuclide metal chelating site on the antibody per se resulting in loss of the label during administration to the patient. In the instant invention, the first complexing site of the chelating compound "out-competes" nonspecific binding sites for the radionuclide metal on the antibody. The complex so formed then transfers the radiometal to the strong chelating site (during incubation at room temperature or with the application of heat) obviating the problem of nonspecific binding.

Pre-Form Approach

The bifunctional chelating compounds of the instant invention are also suitable for use for radiolabeling proteins according to the pre-form approach. This approach is represented by Formulae 6, 7, and 8 below. The method for radiolabeling proteins, such as antibodies according to this approach, consists of first reacting the radionuclide metal with the chelating compound of the instant invention under conditions where the radionuclide metal rapidly forms a complex at the first weak binding site of the chelating compound. The conditions necessary to form this complex are essentially the same as those described above for the post-form approach. The complex so formed may then be incubated at the appropriate temperature, causing an intramolecular rearrangement such that the radionuclide metal ultimately resides at the second site of the chelating compound, thereby forming a stable radionuclide metal-chelate. This stable radionuclide metal-chelate is then admixed with the antibody under conditions suitable for conjugation, resulting in a thermodynamically stable radionuclide metal-chelate-antibody conjugate.

6.
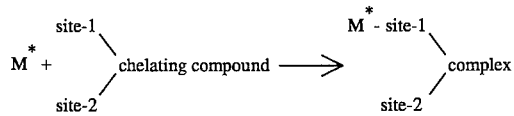

7.
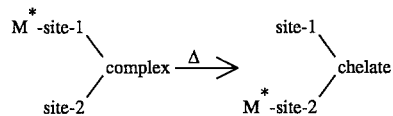

8.
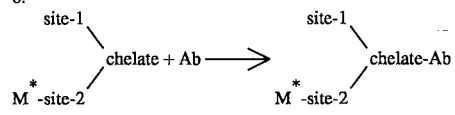

One advantage of employing bifunctional chelating compounds of the instant invention according to the pre-formed approach is that the stable radionuclide metal-chelate complex can be formed at a lower temperature compared to most prior art compounds. This obviates the necessity of heating the metal chelate reaction mixture to elevated temperatures (e.g., on the order of 75° C.). This is particularly advantageous in that heating may decompose reactive conjugation groups, such as active esters; Michael-type acceptors such as maleimides; activated halides; and isothiocyanates. Incubation at temperatures between room temperature and about 37° C. is more convenient in hospital or clinical laboratories. In addition, compounds of the present invention exhibit good yields in the radiolabeling reaction, presumably because the first site and the second site are physically attached to each other.

The specific methods for binding a radionuclide metal to the antibody via either the pre-formed or post-formed approach described above will depend upon the particular radiometal selected and its normal valence. Suitable procedures are known to those skilled in the art.

As discussed above, pertechnetate and perrhenate are contacted with a reducing agent to generate $^{99m}$Tc and $^{188}$Re, respectively, in an oxidation state suitable for complex formation. The pertechnetate or perrhenate may be contacted with the reducing agent in a reaction mixture which also comprises a chelating compound so that the radionuclide metal is quickly bound in the form of a complex before the radionuclide metal can return to its oxidized state. An alternative procedure which may be used when a particular chelating compound (or a protein attached thereto) may be adversely affected by contact with the reducing agent involves preparation of an initial exchange complex. The exchange complex is prepared by reducing pertechnetate or perrhenate in the presence of a separate complexing molecule (e.g., stannous gluconate for $^{99m}$Tc or stannous citrate for $^{188}$Re) to form $^{99m}$Tc-gluconate or $^{188}$Re-citrate exchange complexes, respectively. The exchange complex is contacted with a chelating compound of the invention, whereupon the radionuclide metal is transferred to the first site, and ultimately becomes chelated at the second site.

The subject radionuclide metal-chelate-protein conjugates will be administered to the mammalian host, normally by injection, intravenously, intraarterially, peritoneally, intratumorally, or the like, depending upon the particular site at which the radionuclide metal is desired. Generally, from about 0.1 to 2 mL will be injected into a host for diagnostic purposes, depending upon the size of the host, with about 0.001 to 50 uCi/kg of host. For human hosts the dosage will usually be about 10–50 mCi/70 kg host, more usually about 25–35 mCi/70 kg host. When the radionuclide metal-chelate-protein conjugates are to be injected into the bloodstream of a human, the total volume injected may be larger; e.g., 20 to 30 mL administered by intravenous infusion. For lower mammals (e.g., mice), about 1 to 50 uCi is administered for biodistribution studies, while up to or greater than 500 uCi is administered for imaging studies. After administration of the radionuclide metal-chelate-protein conjugate, depending upon its purpose, the host may be treated in various ways for detection or therapy.

The diagnostic uses of the radionuclide metal-chelate-protein conjugates of the invention thus provide a method for detecting the presence or absence of a particular target site within a human or mammalian host. In general, such a conjugate is administered to the host, and the biodistribution of the $^{99m}$Tc is detected after waiting a predetermined length of time to allow accumulation of the compound at the target site. The diagnostic procedures may vary according to the protein component of the conjugate and other factors.

Technetium-99m ($^{99m}$Tc) has a physical half-life of 6 hours. Whole immunoglobulins have a biological half-life in serum of approximately 24 hours (wide range), and thus the clearance of $^{99m}$Tc-labeled antibody from the circulation is slow compared to the physical half-life of $^{99m}$Tc. A $^{99m}$Tc-labeled F(ab')$_2$ fragment has a shorter circulation time (T ½ 9–20 hours) than whole immunoglobulin, which is more compatible with tumor localization and background clearance for the $^{99m}$Tc-labeled antibody fragment to provide sufficient tumor:background ratios to image lesions successfully. Smaller fragments such as Fab', Fab, and F$_v$ have shorter circulation times (T ½ less than 180 minutes) that are more compatible with the physical T ½ of $^{99m}$Tc and are thus preferred for imaging applications. Choice of molecular species of antibody for imaging with other radionuclide metals will similarly depend on the relationship of the physical half-life of the radionuclide metals and the circulation time of the molecular species of antibody.

Choice of molecular species of antibody for therapy applications of radionuclide metals is more complex. In addition to physical and biological half-lives, residence time of the labeled antibody in the tumor, energy of the emission, and contribution of total body to specific organ dose are critical issues that dictate the optimal size of antibody or fragment. With monoclonal antibodies, the particular antibody will also be a factor influencing the choice.

$^{188}$Re has a 17-hour physical half-life, for which F(ab')$_2$ and Fab antibody fragments have suitable serum half-lives for tumor localization and background clearance. The $^{188}$Re-labeled Fab would be expected to cause less toxicity to the bone marrow, but it will usually have a shorter residence time in tumor due to the lower affinity of univalent compared to bivalent fragments. A $^{188}$Re-labeled Fab fragment with a suitably high affinity to maximize tumor residence of the delivered counts is especially useful.

$^{186}$Re has a 3.67 day physical half-life. It can be used with whole antibody or F(ab')$_2$ or smaller fragments thereof. Because the beta energies are decreased compared to $^{188}$Re, the labeled antibody will need to have a longer residence time in the tumor.

$^{109}$Pd has a half-life of 14 hours. Antibody fragments, as opposed to whole antibodies, are expected to generally be most suitable for radiolabeling in accordance with the invention.

$^{212}$Pb has a physical half-life of 10.8 hours. Fab', Fab, or F$_v$ fragments radiolabeled with $^{212}$Pb would provide the greatest tumor uptake and background clearance in that period. $^{212}$Pb decays to $^{212}$Bi, which has an alpha emission with a physical half-life of 60 minutes. $^{212}$Bi itself is not a feasible label unless compartmental administration (e.g., intraperitoneal) is used. $^{212}$Pb will transmute to $^{212}$Bi in situ, and it is necessary to use a ligand that can withstand the recoil from B-decay.

$^{67}$Cu has a physical half-life of 2.44 days. In general, whole antibodies or F(ab')$_2$ fragments thereof are most suitable for radiolabeling with this isotope for therapeutic use.

Delivery of the radionuclide metal-chelate-antibody conjugate may occur intravenously or by intraperitoneal, intralymphatic, intrathecal, or other intracavitary routes. Advantageously, an unlabeled (nonradiolabeled) antibody reactive with the same epitope as a radiolabeled antibody of the invention is administered prior to administration of the radiolabeled antibody, as described in copending U.S. patent application Ser. No. 917,176, filed Oct. 9, 1986, entitled "Methods for Improved Targeting of Antibody, Antibody Fragments, and Conjugates Thereof." The nonradiolabeled antibody functions as an "unlabeled specific blocker" to decrease binding of the later-administered radiolabeled antibody to cross-reactive sites that may be present on nontarget tissue. Blocking of such cross-reactive sites is important because antibodies generally have some cross-reactivity with tissues other than a particular target tissue. In the case of antibodies directed again tumor-specific antigens, for example, virtually all such antibodies have some cross-reactivity with normal (i.e., nontumor) tissues, with the exception of anti-idiotypes to B-cell lymphoma.

The unlabeled (cold) specific blocker protein advantageously is administered from about 5 minutes to about 48 hours, most preferably from about 5 minutes to about 30 minutes, prior to administration of the radionuclide metal-chelate-protein conjugate. The length of time may vary according to such factors as the nature of the antibody and the relative accessibility of target sites versus cross-reactive binding sites. The unlabeled specific blocker and the radionuclide metal-chelate-antibody conjugate may be the same (except for the radiolabeling) or different, as long as both recognize the same epitope. In one embodiment of the invention, the unlabeled specific blocker is a bivalent form of an antibody (e.g., a whole antibody or a F(ab')$_2$ fragment thereof) and the radiolabeled polypeptide is a monovalent fragment of the same antibody (e.g., a Fab', Fab, or F$_v$ fragment). Use of a bivalent form of an antibody as the cold specific blocker and a monovalent form for the radiolabeled antibody has the advantage of minimizing displacement of the blocker from cross-reactive sites by the later administered radiolabeled antibody due to the greater affinity of the bivalent form. The unlabeled specific blocker polypeptide is administered in an amount effective in binding with (blocking) at least a portion of the cross-reactive binding sites in a patient. Thus, binding of a radiolabeled polypeptide to cross-reactive binding sites may be reduced, thereby improving diagnostic imaging of target sites and, in general, reducing somewhat the amount of radiolabeled antibody to be administered. The amount may vary according to such factors as the size of the patient and the nature of the polypeptide. In general, about 5 mg or more of the unlabeled specific blocker is administered to a human.

Advantageously, a second antibody, termed an "irrelevant" antibody, is also administered to a patient prior to administration of the radiolabeled polypeptide, as described in U.S. patent application Ser. No. 917,176. The irrelevant antibody is an antibody that does not bind to sites within the patient by a specific (e.g., antigen-binding) mechanism but which may bind to target and nontarget sites through nonspecific mechanisms (e.g., adsorption or binding of the Fc portion of the irrelevant antibody to Fc receptors on cells in the reticuloendotheial system). The irrelevant antibody blocks certain nontarget sites in a patient and thus decreases nonspecific binding of the radiolabeled polypeptide to these nontarget sites. Diagnostic imaging of target sites thus may be improved, and the amount of radiolabeled antibody to be administered may be somewhat reduced. For example, prior administrations of an irrelevant antibody that is not specific for any human tissues, as far as is known, effectively reduced the nonspecific uptake of whole and F(ab')$_2$ radiolabeled antibody into liver and spleen in human patients.

The irrelevant antibody advantageously is administered from 5 minutes to 48 hours, most preferably from 15 minutes to one hour, prior to administration of the radiolabeled polypeptide. The length of time may vary according to such factors as the nature of the antibody. Many suitable antibodies that may be used as the irrelevant antibody are known. For example, there are many known antibodies that are not specific for any human tissues that may be used as the irrelevant antibody. In one embodiment of the invention, a murine monoclonal antibody to a B-cell lymphoma idiotype (i.e., specific only for the lymphoma cells of one individual human) is administered as the irrelevant polypeptide. In one embodiment of the invention, the irrelevant polypeptide is a whole antibody or a F(ab')$_2$ fragment thereof. The irrelevant polypeptide is administered in an amount effective in blocking at least a portion of the sites at which nonspecific binding (i.e., binding through nonspecific mechanisms) of the radiolabeled polypeptide occurs in the absence of the irrelevant polypeptide. The amount may vary according to such factors as the nature of the polypeptides and the size of the patient. In general, about 15 mg or more (preferably less than 200 mg) of the irrelevant antibody is administered.

The instant invention also includes a kit for producing radionuclide metal-chelate-protein conjugates comprising a bifunctional chelating compound of the instant invention, and a protein to be radiolabeled. The protein may be any of the above-described proteins which, in radiolabeled form, have diagnostic or therapeutic applications. In one embodiment of the invention, the protein of the instant kit is an antibody, preferably a monoclonal antibody such as a monoclonal antibody specific for cancer cells. In an alternative embodiment of the present invention, the kit includes a protein having a chelating compound of the invention conjugated thereto.

Reagents useful in reactions to radiolabel the chelating compound with a radionuclide metal and to conjugate the chelate compound to the polypeptide according to either the pre-form or post-form approach may also be included. Such kits also may comprise a means for purifying the radiolabeled polypeptide from the reaction mixture, as well as specific instructions for producing the radiolabeled polypeptide using the kit components. Such kits generally will be used in hospitals, clinics, or other medical facilities. Since such facilities generally have ready access on a daily basis to radionuclide metals, such as isotopes of technetium, and since isotopes of rhenium, lead, bismuth, palladium, and copper may be prepared as described above, inclusion of the radionuclide metal in the kit is optional. Exclusion of the radionuclide metal permits storage of the kit, whereas kits containing the radionuclide metal (either as a separate component or as the radiolabeled chelate compound) would have to be used within a narrow time frame (depending on the half-life of the particular isotope); otherwise, radioactive decay of the radioisotope would diminish the effectiveness of the diagnostic or therapeutic technique for which the radiolabeled protein is used. For $^{186}$Re, on-site radiolabeling would avoid radiolytic degradation of the labeled antibody due to the beta particle emission.

The kits may be diagnostic or therapeutic kits, depending on which radioisotope is used for labeling the chelating agent. When the radionuclide metal is to be reduced to a lower oxidation state (e.g., technetium and rhenium, as discussed above), the kits may additionally comprise a reducing agent effective in reducing a particular radionuclide metal, to be chelated by the chelating compound, to an oxidation state at which a complex of the radionuclide metal-chelate may be formed.

The bifunctional chelating compounds may be radiolabeled with a radionuclide metal prior to or after conjugation to a protein. A kit suitable for use in the pre-formed approach preferably includes a bifunctional chelating compound comprising sulfur-protecting groups and a protein in separate containers. A kit suitable for use in the post-form approach may contain the bifunctional chelating compound and the protein in separate containers, for conjugation at a later time, or the chelating compound may already be conjugated to a protein. The term "separate containers" as used herein is meant to include not only separate, individual containers (e.g., vials) but also physically separate compartments within the same container. Bifunctional chelating compounds of the instant invention are preferably already conjugated to a protein.

In accordance with one embodiment of the invention, a diagnostic kit suitable for use according to the post-form approach comprises the following reagents (in separate containers unless otherwise noted), presented in the general order of use.

1. A reducing agent effective in reducing pertechnetate ($^{99m}$TcO$_4$) to a lower oxidation state at a neutral to acidic pH so that a technetium-chelate complex can be formed. Many suitable reducing agents are known, including but not limited to, stannous ion, (e.g., in the form of stannous salts, such as stannous chloride or stannous fluoride), metallic tin, formamidine sulfinic acid, ferric chloride, ferrous sulfate, ferrous ascorbate, and alkali salts of borohydride. Preferred reducing agents are stannous salts.

2. A chelating compound of the invention conjugated to a protein or fragment thereof specific for the desired target organ, tissue, antigen, or other target site within a mammalian body, as discussed above.

3. Means for purifying the desired radionuclide metal-chelate-protein conjugate from the reaction mixture. Any suitable known protein purification technique may be used that effectively separates the desired radiolabeled protein conjugate from other compounds in the reaction mixture. The purification step may, for example, separate the desired conjugate from impurities due to differences in size or in electrical charge. One suitable purification method involves column chromatography, using, for example, an anion exchange column or a gel permeation column. Good results are also achieved by column chromatography using an anion exchange column, e.g., a quaternary aminoethyl Sephadex (QAE-Sephadex) column or a diethylaminoethyl Sephadex (DEAE-Sephadex) column. Since virtually all the impurities to be removed (e.g., sodium pertechnetate and technetium dioxide), are negatively charged, they are substantially retained on the positively charged column. Purification thus may be accomplished by this one-step column procedure.

4. Additional reagents for use in the radiolabeling the protein-chelate conjugate (e.g., the buffers, alcohols, acidifying solutions, and other such reagents, as described below) are generally available in medical facilities and thus are optional components of the kit. However, these reagents preferably are included in the kit to ensure that reagents of sufficient purity and sterility are used because the resulting radionuclide metal-chelate-protein conjugates are to be administered to mammmals, including humans, for medical purposes.

5. Optionally, a container of a polypeptide to be administered in nonradiolabeled form to a human or mammal is included in the kit. This polypeptide is reactive with essentially the same target site as the polypeptide to be radiolabeled and reduces binding of the radiolabeled polypeptide to cross-reactive binding sites on nontarget tissues. The two polypeptides may be the same, or the polypeptide to be radiolabeled may, for example, be a fragment of the polypeptide that is to be administered In nonradiolabeled form. The latter polypeptide is administered as an unlabeled specific blocker (prior to administration of the radiolabeled polypeptide) in an amount effective in improving diagnostic imaging of the desired target sites (e.g., tumors), as described above.

6. Optionally, the kit also comprises a container of a polypeptide that does not bind through specific mechanisms to sites within the human or mammal to which the radiolabeled polypeptide is to be administered. This polypeptide is administered as an "irrelevant" polypeptide (prior to administration of the radiolabeled polypeptide) in an amount effective in decreasing nonspecific uptake of certain radiolabeled polypeptides, as described above.

The following specific examples are intended to illustrate more fully the nature of the present Invention without acting In any way to limit its scope.

EXAMPLE I

Figure 1B:
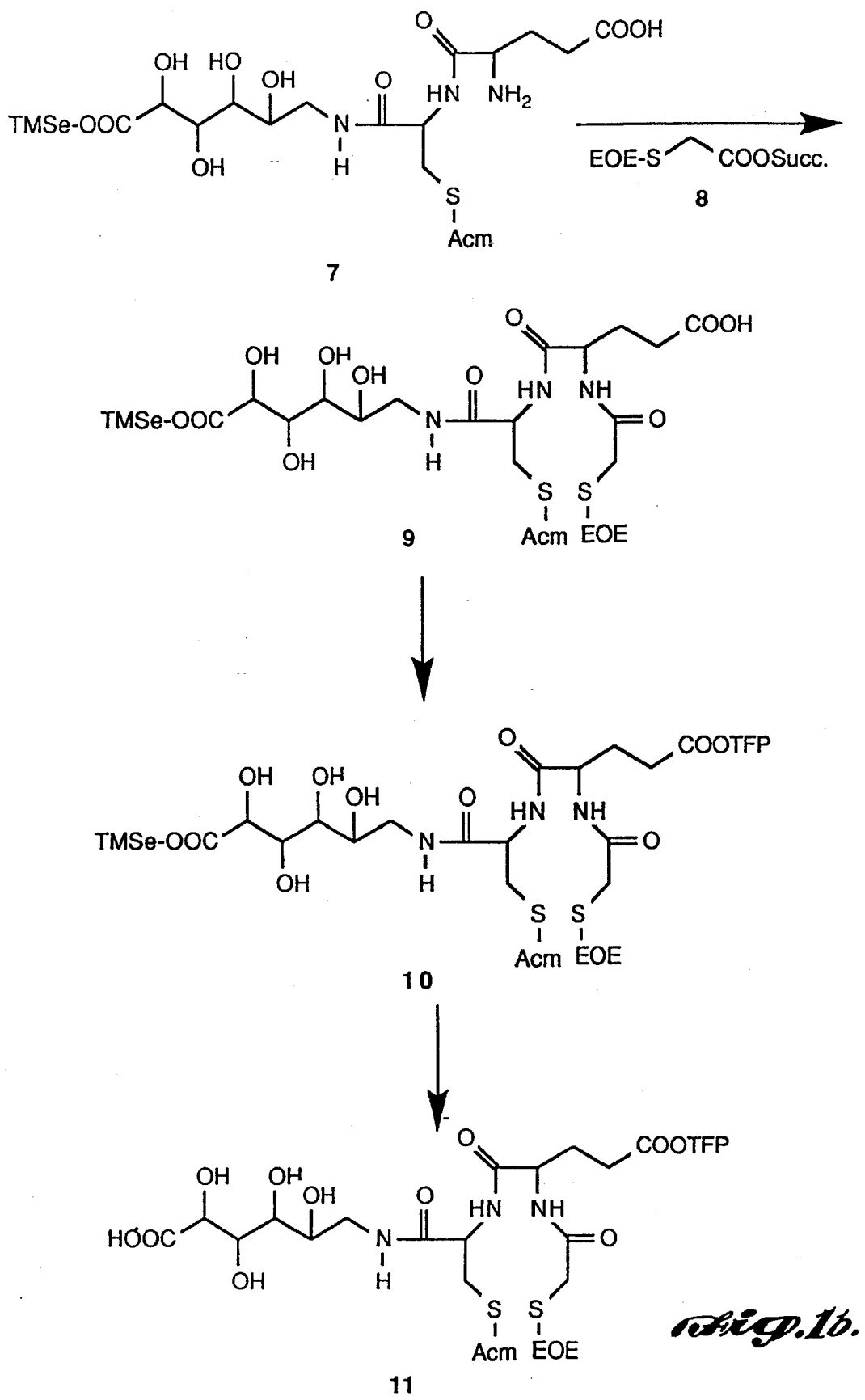

Synthesis of a diamidodimercapto bifunctional anchimeric chelate
N-(S-1-ethoxyethylmercaptoacetyl)-γ-(2,3,5,6,-tetrafluorophenoxy)L-glutamyl-α-S-acetamidomethyl-L-cysteinyl-6-amino-6-deoxy-D-gluconic acid The following synthesis is best understood by referring to FIGS. 1a and 1b.

N-(t-butoxycarbonyl)-γ-(t-butoxy)-L-glutamyl-S-acetamidomethyl-L-cysteine 3: A solution of S-(acetamidomethyl)-L-cysteine (2 mmol) 1 in 10 mL of anhydrous dimethylformamide containing 4-dimethylaminopyridine (2 mmol) is cooled in an salt-ice bath to 0°–5° C. To this solution is added previously cooled isobutylchloroformate (2 mmol), and the solution is incubated at this temperature for another 30 minutes. A solution of N-(t-butoxycarbonyl)-L-glutamic acid-γ-butyl ester 2 (2 mmol) in 5 mL of dimethylformamide is added at such a rate that the temperature of the reaction mixture does not exceed 0° C.

The mixture is kept at this temperature for another 1 hour and allowed to come to room temperature. The solution is extracted with 2×20 mL of methylene chloride and dried over anhydrous sodium sulfate. Evaporation and crystallization give the dipeptide derivative 3.

N-(t-butoxycarbonyl)-γ-(t-butoxy)-L-glutamyl-S-acetamidomethyl-L-cysteinyl-6-amino-6-deoxy-D-gluconic acid 5:

(i) A solution of 3 (1 mmol) in 10 mL of anhydrous tetrahydrofuran is stirred with 1.1 mmol of N-hydroxysuccinimide and 1.1 mmol of N,N'-dicyclohexylcarbodiimide. After stirring overnight the precipitated dicyclohexylurea is filtered and the filtrate is evaporated to dryness. The residue is dissolved in 20–25 mL of ethyl acetate and washed with water, and the organic layer is dried over anhydrous sodium sulfate. Evaporation and crystallization give the succinimidate ester as a solid.

(ii) To a solution of the above ester (1 mmol) in a mixture of 1:1 acetonitrile:water, 6-amino-6-deoxy-D-gluconic acid 4 (prepared from 1,2-O-isopropylidine-α-D-glucopyranose according to the procedure of K. Kefurt et. al., *Collection Czecholslov. Chem. Comm.*, 44, 2526 (1979)) is added, and the mixture is stirred for 6 hours at room temperature. The product 5 is isolated by evaporation followed by flash chromatography over silica gel.

N-(t-butoxycarbonyl)-γ-(t-butoxy)-L-glutamyl-S-acetamidomethyl-L-cysteinyl-6-amino-6-deoxy-D-gluconic acid trimethylsilylethyl ester 6: To 5 mL of a solution containing 1 mmol of the above acid 5, anhydrous dimethylformamide, and 1 mmol of N-methylmorpholine maintained at 0°–5° C., 1 mmol of isobutylchloroformate is added, and the mixture is kept at this temperature for 20 minutes. To this solution is added a solution of 1 mmol of trimethylsilylethanol in 2 mL of anhydrous dimethylformamide (previously cooled to 0°–5° C.), and the solution is stirred for 1 hour at this temperature and allowed to come to room temperature. The solvent is removed in vacuo and the residue is dissolved in 20 mL of ethyl acetate and washed with water. The organic layer is dried and evaporated to give 6.

L-glutamyl-α-S-acetamidomethyl-L-cysteinyl-6-amino-6-deoxy-D-gluconic acid trimethylsilylethyl ester 7: The above ester (1 mmol) is dissolved in 5 mmol of anhydrous trifluoroacetic acid (previously cooled to 0° C.) and stirred for 3 hours. The solution is allowed to come to room temperature and is evaporated in vacuo. Trituration with ether yields the amino acid 7 as the trifluoroacetate salt.

N-(S-1-Ethoxyethylmercaptoacetyl)-L-glutamyl-α-S-acetamidomethyl-L-cysteinyl-6-amino-6-deoxy-D-gluconic acid trimethylsilylethyl ester 9: Reagent 8 is prepared by first preparing S-(1-ethoxyethyl)mercaptoacetic acid 16 (as described below).

The S-(1-ethoxyethyl)mercaptoacetic acid (5.76 g, 35.1 mmol) is combined with N-hydroxysuccinimide (4.85 g, 42.1 mmol) in 100 mL of anhydrous THF. To this is added a solution of 1,3-dicyclohexylcarbodiimide (8.70 g, 42.1 mmol) in 65 mL of anhydrous THF. The mixture is stirred at room temperature for 2 hours, or until TLC analysis indicates complete formation of the succinimidyl ester. The mixture is then filtered, and the filtrate is concentrated in vacuo to a viscous residue. The residue is dissolved in ethyl acetate, washed with water, brine, and dried (MgSO₄).

Removal of the solvent leaves the crude succinimidyl ester as an oil, which is further purified by flash chromatography on silica gel, using ethyl acetate:hexanes as the column eluant, to give 5.1 g of S-1-ethoxyethylmercaptoacetic acid succinimidyl ester 8 as a colorless oil.

To a solution of 7 (1 mmol) in 10 mL of anhydrous dimethylformamide containing 1 mmol of triethylamine, 1 mmol of S-(1-ethoxyethyl)mercaptoacetic acid succinimidate ester 8 is added and the solution is stirred for three hours at ambient temperature. The solvent is removed in vacuo, and the residue is dissolved in ethyl acetate and washed with water. The organic layer is dried and evaporated, and the product is purified by flash chromatography to give the product 9.

N-(S-1-Ethoxyethylmercaptoacetyl)-γ-(2,3,5,6,-tetrafluorophenoxy)L-glutamyl-α-S-acetamidomethyl-L-cysteinyl-6-amino-6-deoxy-D-gluconic acid trimethylsilylethyl ester 10: To a solution of 9 (1 mmol) in 20 mL of anhydrous tetrahydrofuran, 2,3,5,6-tetrafluorophenol and N,N'-dicyclohexylcarbodiimide is added, and the solution is stirred for 10–12 hours at room temperature. The precipitated dicyclohexylurea is filtered, and the solvent is removed by evaporation under reduced pressure. The residue is dissolved in 20–30 mL of ethyl acetate and washed with water. The organic layer is dried and evaporated, and the product 10 is isolated by flash chromatography over silica gel.

N-(S-1-Ethoxyethylmercaptoacetyl-γ-(2,3,5,6-tetrafluorophenoxy)L-glutamyl-α-S-acetamidomethyl-L-cysteinyl-6-amino-6-deoxy-D-gluconic acid 11: To a solution of 1 mmol of 10 in 10 mL of anhydrous tetrahydrofuran, 3 mL of 1M tetra-n-butylammonium fluoride is added, and the solution is stirred for 6–8 hours at ambient temperature. The solvent is removed by evaporation, and the product 11 is isolated by flash chromatography.

EXAMPLE II

Figure 2A:
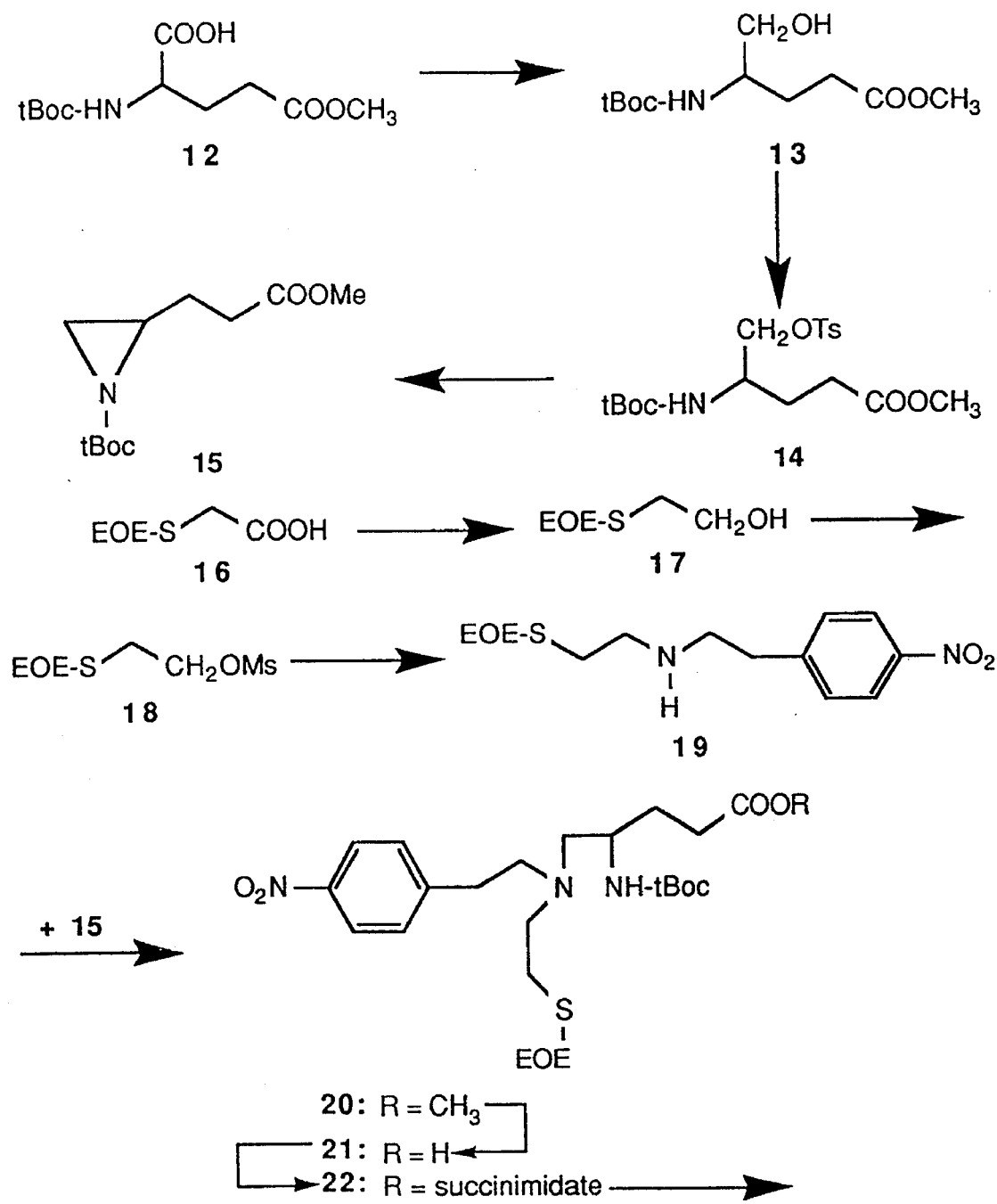
FIGS. 2a and 2b illustrate the pathway for the synthesis of a bifunctional amido amino dimercapto anchimeric chelate.
Figure 2B:
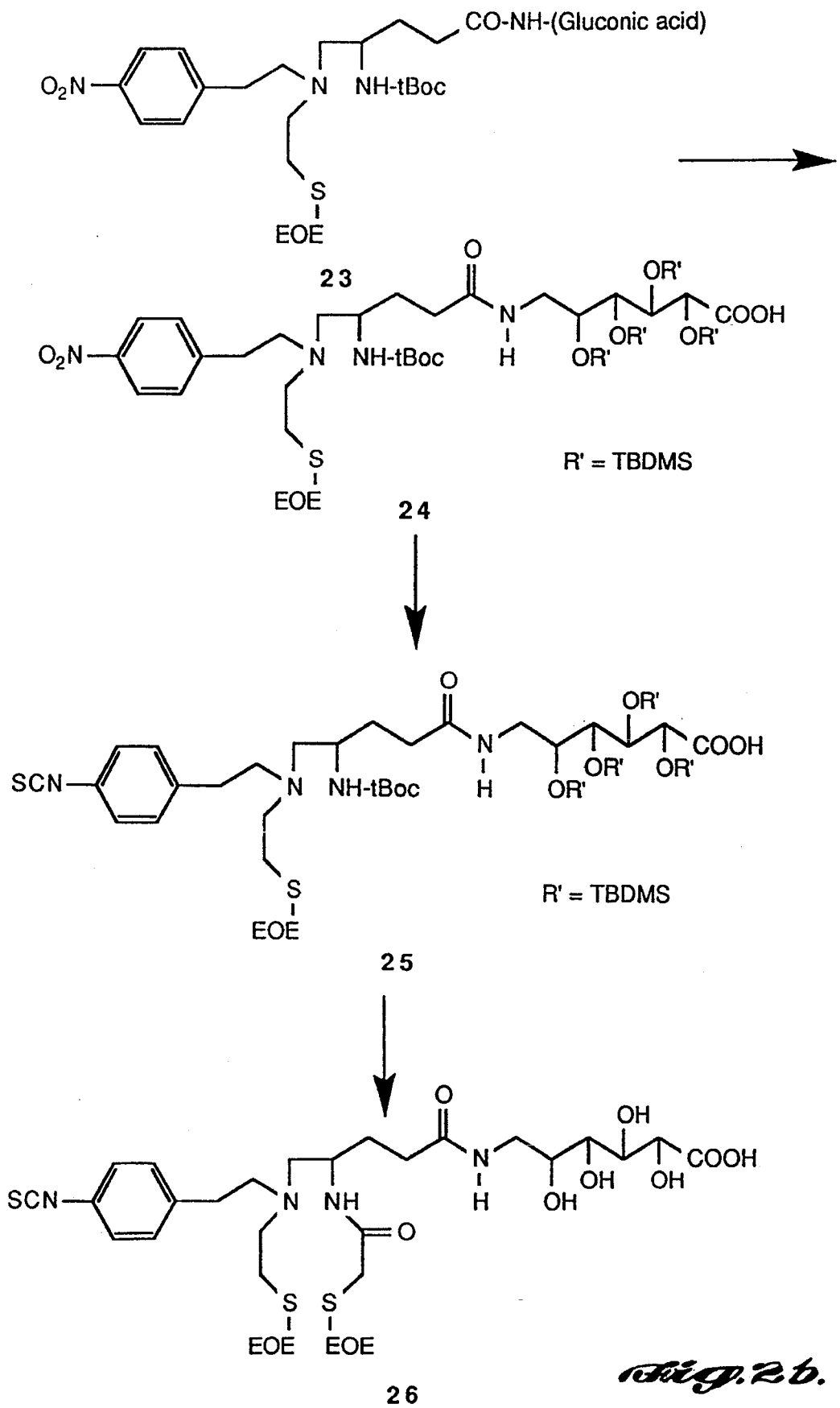

Synthesis of an amino amido dimercapto bifunctional anchimeric chelate 4-N-(S-1-ethoxyethylmercaptoacetyl)-5-N'-(p-isothiocyanatophenethyl)-N'-β-(S-1-ethoxyethyl)mercaptoethyl-diaminopentanoyl-6'-amino-6'-deoxy-D-gluconic acid The following synthesis is best understood by referring to FIGS. 2a and 2b.

N-t-Butoxycarbonyl-β-carbomethoxyethyl aziridine 15:

(i) N-t-butoxycarbonyl-L-glutamic acid-γ-methyl ester 12 is prepared from L-glutamic acid-γ-methyl ester according to the procedure of R. K. Olsen and T. Emery., *J. Org. Chem.*, 49:3527 (1984).

(ii) A 1.0M solution of borane:THF (0.68 mL, 0.68 mmol) was added to a solution of 12 (143 mg. 0.55 mmol) in anhydrous tetrahydrofuran (0.68 mL). The reaction solution was stirred at ambient temperature for one hour and then quenched by the addition of 10 mL of methanol. The reaction solution was then evaporated to give an oil (160 mg). The oil was dissolved in 70 mL of ethyl acetate and washed with saturated NaHCO₃ (2×30 mL). The organic layer was dried over anhydrous MgSO₄ and evaporated in vacuo to give 13 as a colorless oil (120 mg, 88%).

(iii) p-Toluenesufonyl chloride (0.85 g, 4.45 mmol) was added to an ice cold (0°–5° C.) solution of 13 (1.00 g, 4.05 mmol) in pyridine (8 mL). The reaction solution was stirred at this temperature overnight. The reaction solution was diluted with methylene chloride (80 mL) and washed with pH 4.0 buffer (3×70 mL), then with saturated bicarbonate (40 mL). The organic extract was repeatedly evaporated from toluene (to azeotrope the pyridine), giving the tosylate 14 as a brown viscous oil that was used in the next step without further purification.

(iv) A solution of the tosylate 14 (1.38 g) in anhydrous dimethylformamide (3.0 mL) was added to a suspension of NaH (95 mg, 3.78 mmol) in DMF (1.5 mL). The reaction mixture was stirred for 1 hour, diluted with water (40 mL), and extracted with methylene chloride (3×40 mL). The combined methylene chloride extracts were dried ($MgSO_4$) and evaporated to give a yellow oil (0.66 g). The oil was purified by flash chromatography over silica gel (1:1 ethyl acetate:hexanes) to give 15 as a pale yellow oil.

(S-1-Ethoxyethyl)-N-(p-nitrophenethyl)mercaptoethylamine 19:

(i) S-(1-ethoxyethyl)mercaptoacetic acid 16 was prepared according to the following procedure: A solution of mercaptoacetic acid (17.4 mL, 250 mmol) in 125 mL of dichloromethane containing p-toluenesulfonic acid monohydrate (0.24 g, 1.26 mmol) was cooled to −18° to −25° C. with stirring. Ethyl vinyl ether (23.9 mL, 250 mmol) in 125 mL of dichloromethane was added dropwise to the cold solution over a period of 90 minutes. The stirring was continued for an additional 30 minutes, with the temperature maintained in the −18° to −25° C. range. Then 200 mL of pH 7 phosphate buffer was added, and the reaction mixture was allowed to warm with stirring for 10 to 15 minutes. The mixture was then poured into a flask containing 900 mL of ethyl acetate and 200 mL of water. Layers were separated, and the aqueous portion extracted twice with ethyl acetate. The organic layers were combined, washed with brine, and dried ($MgSO_4$). Removal of the solvent left 31.4 g of S-(1-ethoxyethyl)mercaptoacetic acid 16 as a colorless oil (77% yield): $^1$H NMR ($CDCl_3$) 1.15(t,J=7.0 Hz,3H), 1.52(d,J=6.4 Hz,3H), 3.36(s,2H), 3.60(m,2H), 4.84(q,J=6.4 Hz, 1H), 11.65(s, 1H). The material was used without further purification.

(ii) To a solution of 3.07 g of 16 in 65 mL of anhydrous tetrahydrofuran (kept at 0° C.) 93.5 mL of borane:THF complex (1M) was added slowly. The mixture was stirred for 7.5 hours in a nitrogen atmosphere at 0° C. Approximately 500 mL of water was added slowly to the reaction mixture and stirred for 15 minutes. The mixture was concentrated under vacuum at 40°–50° C. and the aqueous residue was extracted with ethyl acetate. The ethyl acetate layer was washed with 50 mL of 10% $Na_2CO_3$. The aqueous layer was washed again with 2×25 mL of ethyl acetate. The combined organic layers were washed with brine, dried, filtered, and evaporated to give 1.7 g of an oil. The oil was purified in an HPLC to give 1.34 g of 17 as a colorless oil.

(iii) To a solution of 17 (1 mmol) in 5 mL of methylene chloride containing 1 mmol of triethylamine maintained at 0° C. was added methanesulfonyl chloride (1 mmol) and the solution stirred for one hour at this temperature. The mesylate 18 was unstable and hence the amidation was carried out without isolation.

To the above solution 1.1 mmol of p-nitrophenethylamine is added, and the solution is stirred at this temperature for two hours and allowed to come to ambient temperature. After stirring overnight at room temperature, the solution is diluted with saturated bicarbonate, extracted with methylene chloride. The combined organic extracts are washed with brine, dried over anhydrous $MgSO_4$, and evaporated to give 19 as a viscous oil, which is purified by flash chromatography over silica gel.

4-N-(t-butoxycarbonyl)-5-N'-(p-nitrophenethyl)-N'-β-(S-1-ethoxyethyl)mercaptoethyl-diaminopentanoic acid 21:

(i) To a solution of N-t-butoxycarbonyl-S-carbomethoxyethyl aziridine 15 (1 mmol) in anhydrous tetrahydrofuran (5 mL), is added S-ethoxyethyl-N-(p-nitrophenethyl)mercaptoethylamine 19, and the mixture is refluxed for 6–8 hours. The solvent is removed in vacuo, and the product 20 4-N-(t-butoxycarbonyl)-5-N'-(p-nitrophenethyl)-N'-β-(S-ethoxyethyl)-mercaptoethyl-diaminopentanoic acid methyl ester is used in the next step without further purification.

(ii) To a solution of the above compound (1 mmol in 5 mL of methanol), 0.7 mL of 2N NaOH is added, and the mixture is stirred for overnight at room temperature. The solution Is concentrated to a small volume and acidified to pH 2–3 with 0.5N HCl. The precipitated solid 21 is collected by filtration and purified by flash chromatography over silica gel and crystallization.

4-N-(t-butoxycarbonyl)-5-N'-(p-nitrophenethyl)-N'-β-(S-1-ethoxyethyl)-mercaptoethyl-diaminopentanoyl-6'-amino-6'-deoxy-D-gluconic acid 23:

(i) A solution of 21 (1 mmol) in 15 mL of anhydrous tetrahydrofuran is stirred with 1.1 mmol of N-hydroxysuccinimide and 1.1 mmol of N,N'-dicyclohexylcarbodiimide. After stirring overnight at room temperature, the precipitated solid is filtered and the solution evaporated. The residue is dissolved in 2×20–25 mL of ethyl acetate and washed with water. The organic layer is dried over anhydrous $Na_2SO_4$ and evaporated. The product obtained 22 crystallized form ethyl acetate.

(ii) The above succinimidate 22 ester (1 mmol) is dissolved in 20 mL of acetonitrile:water (4:1) to which 1 mmol of 6-amino-6-deoxy-D-gluconic acid 4 is added in one lot, and the mixture is stirred for three hours at room temperature. The solvent is removed in vacuo, and the residue is chromatographed to give the product 23 as a solid.

4-N-(t-butoxycarbonyl)-5-N'-(p-nitrophenethyl)-N'-β-(S-1-ethoxyethyl)-mercaptoethyl-diaminopentanoyl-2',3',4',5'-tetra-O-t-butyldimethylsilyl-6'-amino-6'-deoxy-D-gluconic acid 24: To a solution of 23 (1 mmol) in anhydrous tetrahydrofuran containing triethylamine (5 mmol), t-butyldimethylsilyl chloride is added. The mixture is stirred for 8–10 hours at room temperature. The solvent is evaporated, and the residue is crystallized and dissolved in ethyl acetate (20–30 mL), then washed with brine, dried with anhydrous $Na_2SO_4$, and evaporated to obtain the t-butyldimethylsilyl derivative 24.

4-N-(t-butoxycarbonyl)-5-N'-(p-isothiocyanatophenethyl)-N'-β-(S-1-ethoxyethyl)mercaptoethyl-diaminopentanoyl-2',3',4', 5'-tetra-O-t-butyldimethylsilyl-6'-amino-6'-deoxy-D-gluconic acid 25:

(i) A solution of 24 (1 mmol) in 50 mL of ethanol containing 100 mg of sulfided Pd/C (5%) is shaken in a Paar hydrogenator at a pressure of 60 psi for 15–20 hours. The catalyst is removed by filtration through celite, and the filtrate is evaporated to give the amino compound 4-N-(t-butoxycarbonyl)-5-N'-(p-aminophenethyl)-N'-β-(S-1-ethoxyethyl)mercaptoethyl-diaminopentanoyl-2',3',4',5'-tetra-O-t-butyldimethylsily-6'-amino-6'-deoxy-D-gluconic acid as an oil, which is used in the next step without further purification.

(ii) To a solution of the above amino compound in 25 mL of methylene chloride is added thiocarbonyldiimidazole (1.1 mmol) and the mixture is stirred overnight at room temperature. The solution is diluted with another 20 mL of methylene chloride and washed with water. Evaporation and crystallization give the isothiocyanate 25 as a solid.

4-N-(S-1-ethoxyethylmercaptoacetyl)-5-N'-(p-isothiocyanatophenethyl)-N'-β-(S-1-ethoxyethyl)mercaptoethyl-diaminopentanoyl-6'-amino-6'-deoxy-D-gluconic acid 26

(i) A solution of 25 (1 mmol) is stirred with 5 mL of anhydrous trifluoroacetic acid for 3–4 hours at room temperature. One mL of water is added to the reaction mixture and the mixture is evaporated to give an oily product. This residue is triturated with organic solvent to give the requisite intermediate 5-N-(p-isothiocyanatophenethyl)-N-β-(S-1-ethoxyethyl)mercaptoethyl-4,5-diaminopentanoyl-6'-amino-6'-deoxy-D-gluconic acid.

(ii) To a solution of the above compound (1 mmol) in 5 mL of anhydrous dimethylformamide containing an equimolar amount of triethylamine is added 1.1 mmol of S-1-ethoxyethylmercaptoacetic acid succinimidate ester and the mixture is stirred for 6 hours at room temperature. The solvent is removed in vacuo, and the residue containing the product 26 and N-hydroxysuccinimide is shaken with ethyl acetate to remove the unreacted N-hydroxysuccinimide. The filtered solid is purified by preparative liquid chromatography to give a pure product 26.

EXAMPLE III

Synthesis of a diamino dimercapto bifunctional anchimeric chelate 4-N -methyl-N-β-(S-1-ethoxyethyl)mercaptoethyl-5-N'-(p-thiocyanatophenethyl)-N'-β-(S-1-ethoxyethyl)mercaptoethyl-diaminopentanoyl-6'-amino-6'-deoxy-D-gluconic acid.

Figure 3A:
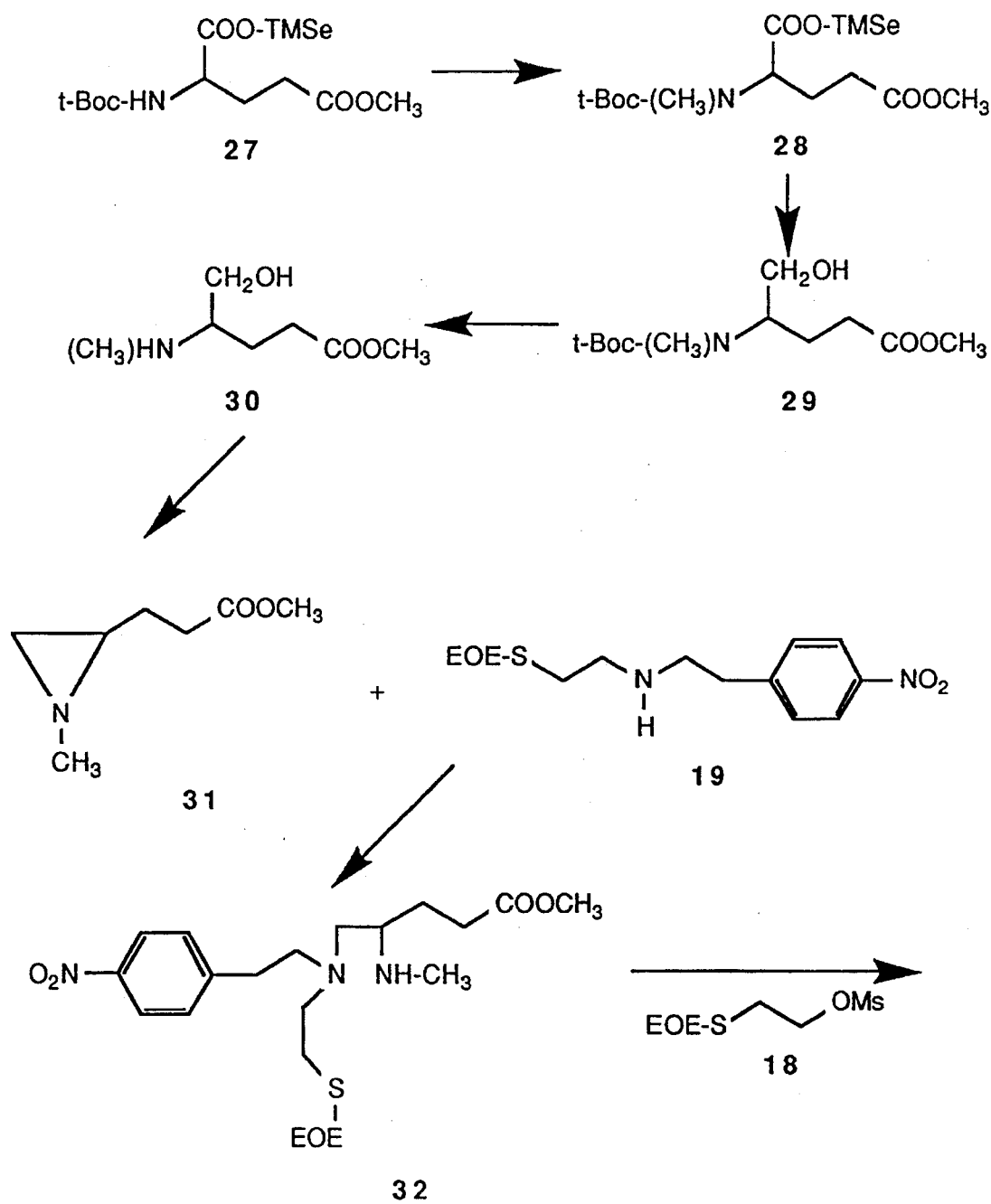
FIGS. 3a and 3b illustrate the pathway for the synthesis of a bifunctional diamino dimercapto anchimeric chelate.
Figure 3B:
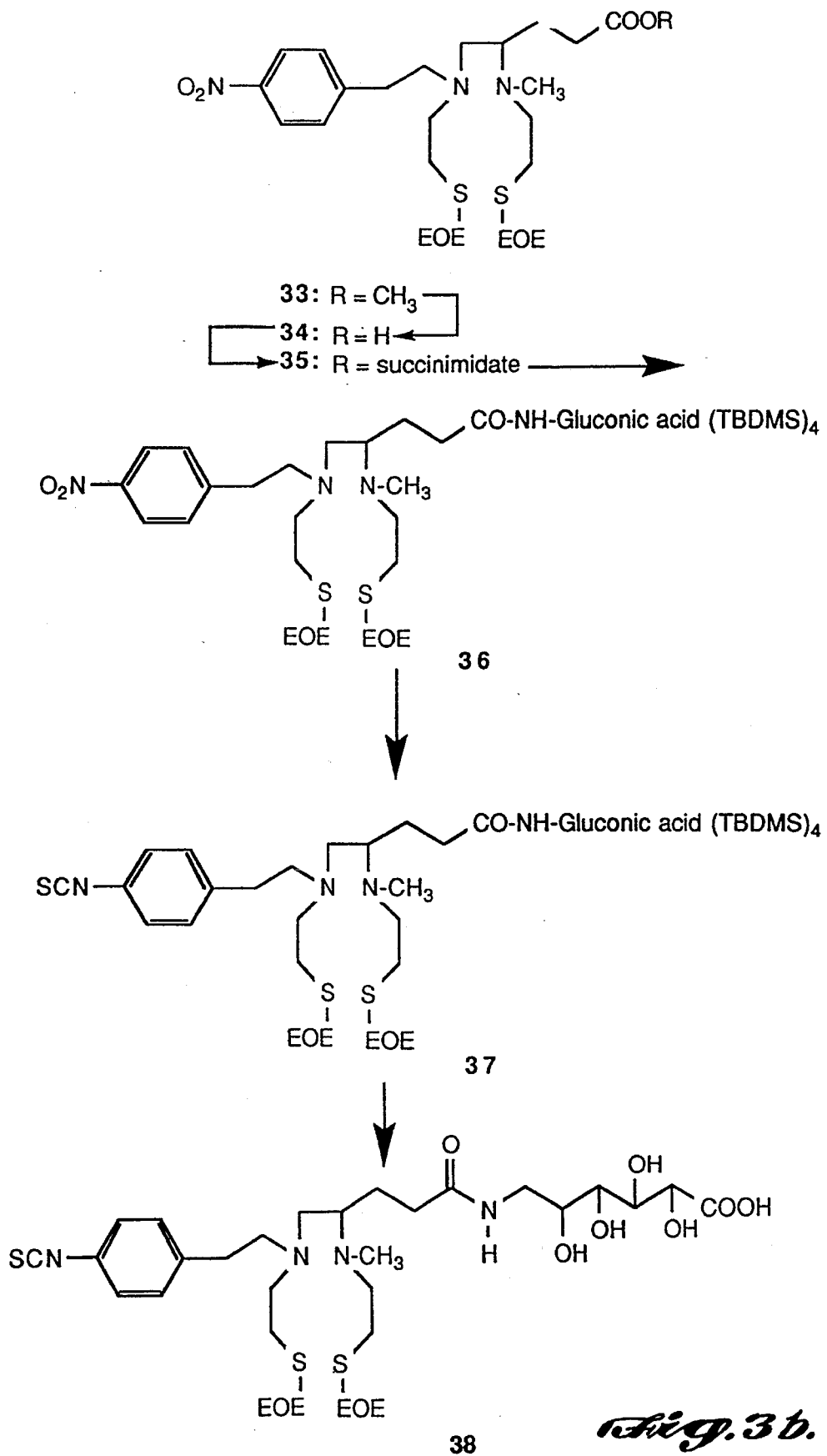

The following synthesis is best understood by referring to FIGS. 3a and 3b.

N-Methyl-β-carbomethoxyethyl aziridine 31:

(i) To a solution of t-butoxycarbonyl-L-glutamic acid-γ-methyl ester 12 (1 mmol) in 10 mL of anhydrous tetrahydrofuran, 1.1 mmol of trimethylsilyl ethanol and 1.1 mmol of N,N'-dicyclohexylcarbodiimide is added, and the solution is stirred overnight. The precipitated solid is filtered, and the filtrate is evaporated. The residue is dissolved in ethyl acetate and washed with water, dried with anhydrous MgSO$_4$, evaporated, and crystallized to give 27 N-t-butoxycarbonyl-L-glutamic acid-(α-trimethylsilylester)-γ-methyl ester.

(ii) To a solution of 27 (N-t-butoxycarbonyl-L-glutamic acid-(α-trimethylsilylester)-γ-methyl ester) (1 mmol) in 10 mL of anhydrous methylformamide, 3 mmol of silver oxide is added, and the mixture is kept at 37°–40° C. After 24 hours at room temperature, the mixture is filtered and evaporated to dryness. The residue is dissolved in CH$_2$Cl$_2$, washed with water, dried, and evaporated to give 28 (N-t-butoxycarbonyl-N-methyl-L-glutamic acid-[α-trimethylsilylester)-γ-methyl ester.

(iii) A solution of 28 (2 mmol) in 10 mL of anhydrous tetrahydrofuran is stirred with 5 mL of 1M tetra-n-butylammonium fluoride for six hours. The solvent is removed, and the residue is washed with water, dried, and evaporated to give N-t-butoxycarbonyl-N-methyl-L-glutamic acid-γ-methyl ester. This compound is converted to the product 4-(t-butoxycarbonyl-methylamino)-4-(hydroxymethyl)-butanoic acid methyl ester 29, in a procedure similar to the one described for the conversion of 12 to 13.

(iv) A solution of 1 mmol of 29 (4-(t-butoxycarbonyl-methylamino)-4-(hydroxymethyl)-butanoic acid methyl ester) is stirred with 5 mL of anhydrous trifluoroacetic acid for two hours and evaporated to dryness. The residue is triturated with ether to give the trifluoroacetate salt 4-(methylamino)-4-(hydroxymethyl)-butanoic acid methyl ester 30.

(v) A solution of 30 (1 mmol) in anhydrous tetrahydrofuran is treated with pyridine SO$_3$-complex (1.1 mmol) to give the O-sulfonate of 30. After TLC shows the disappearance of the starting material, the solution is heated to boiling overnight to give the product 31 (N-methyl-β-carbomethoxyethyl aziridine), which is recovered by removal of the solvent.

4-N-methyl-5-N'-(p-nitrophenethyl)-N'-β-(S-1-ethoxyethyl)mercaptoethyldiaminopentanoic acid methyl ester 32: This compound is prepared from 31 and 19 (S-1-ethoxyethyl-N-(p-nitrophenethyl)mercaptoethylamine) in a procedure similar to the one described earlier for the preparation of 20 from 15 and 19).

4-N-methyl-N-β-(S-1-ethoxyethyl)mercaptoethyl-5-N'-(p-nitrophenethyl)-N'-β-(S-1-ethoxyethyl)mercaptoethyl-diaminopentanoic acid succinimidate ester 34:

(i) A mixture of 33 and 18 (S-ethoxyethyl-β-mercaptoethanol mesylate (EXAMPLE I) in equimolar amounts are heated in 10 mL of anhydrous tetrahydrofuran for six hours. The solvent is removed in vacuo, and the residue is dissolved in ethyl acetate and washed with water. The organic layer is dried and evaporated to give 33, 4-N-methyl-N-β-(S-1-ethoxyethyl)mercaptoethyl-5-N'-(p-nitrophenethyl)-N'-β-(S-1-ethoxyethyl)mercaptoethyl-diaminopentanoic acid methyl ester.

(ii) The above methyl ester 33 is hydrolyzed to the free acid 34 (4-N-methyl-N-β-(S-1-ethoxyethyl)mercaptoethyl-5-N'-(p-nitrophenethyl)-N'-β-(S-1-ethoxyethyl)mercaptoethyl diaminopentanoic acid) in a similar procedure described earlier for the conversion of 20 to 21 (see EXAMPLE I).

(iii) The free acid 34 is converted to the succinimidate ester 35 (4-N-methyl-N-β-(S-1-ethoxyethyl)mercaptoethyl-5-N'-(p-nitrophenethyl)-N'-β-(S-ethoxyethyl)mercaptoethyl diaminopentanoic acid succinimidate ester) in a similar procedure described for the conversion of 21 to 22 (see EXAMPLE I).

4-N-methyl-N-β-(S-1-ethoxyethyl)mercaptoethyl-5-N'-(p-nitrophenethyl)-N'-β-(S-1-ethoxyethyl)mercaptoethyl-diaminopentanoyl-6'-amino-6'-deoxy-2',3',4',5'-tetra-O-t-butyldimethylsilyl-D-gluconic acid 36: Compound 35 is converted to 36 in two successive steps in a procedure similar to the one described earlier for the conversion of 22 to 24 (see EXAMPLE I).

4-N-methyl-N-β-(S-1-ethoxyethyl)mercaptoethyl-5-N'-(p-isothiocyanatophenethyl)-N'-β-(S-1-ethoxyethyl)mercaptoethyl-diaminopentanoyl-6'-amino-6'-deoxy-2',3',4',5'-tetra-O-t-butyldimethylsilyl-D-gluconic acid 37: Compound 36 is converted to 37 in two successive steps in a procedure similar to the one described earlier for the conversion of 24 to 25 (see EXAMPLE I).

4-N-methyl-N-β-(S-1-ethoxyethyl)mercaptoethyl-5-N'-(p-isothiocyanatophenethyl)-N'-β-(S-1-ethoxyethyl)mercaptoethyl-diaminopentanoyl-6'-amino-6'-deoxy-D-gluconic acid 38. Deprotection of 37 to the target compound 38 is achieved by stirring the compound (1 mmol) in 10 mL acetonitrile containing 2 mL of 1N hydrochloric acid for 2–3 hours. Evaporation of the solvent followed by purification by HPLC yields the product 38 in a pure state.

EXAMPLE IV

Figure 4A:
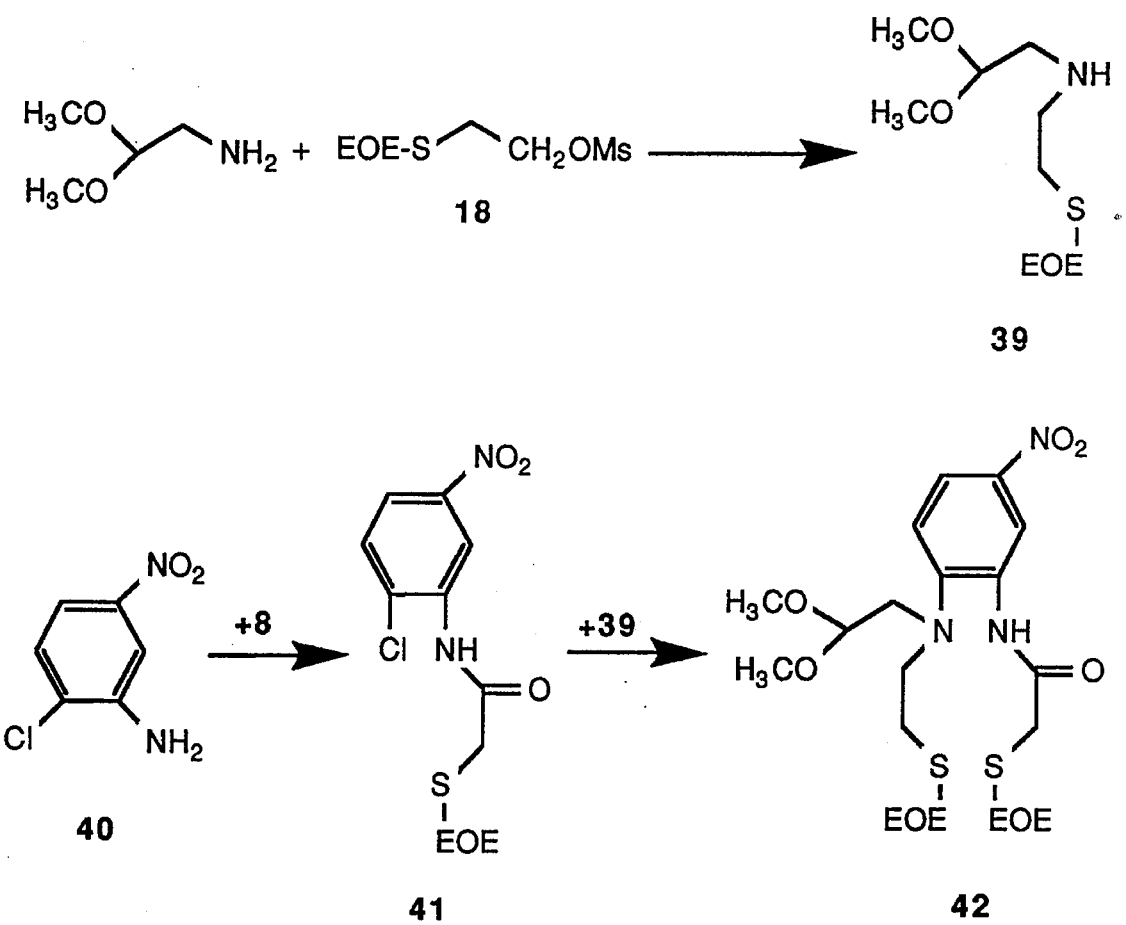
FIGS. 4a and 4b illustrate the pathway for the synthesis of a bifunctional diamidodimercapto anchimeric chelate having an aromatic bridge.
Figure 4B:
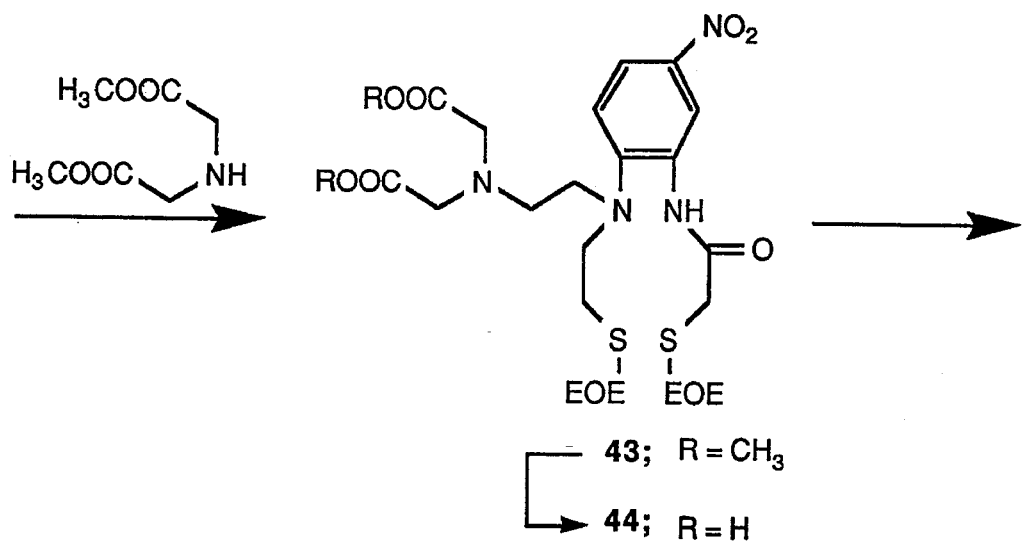
Figure 4B:
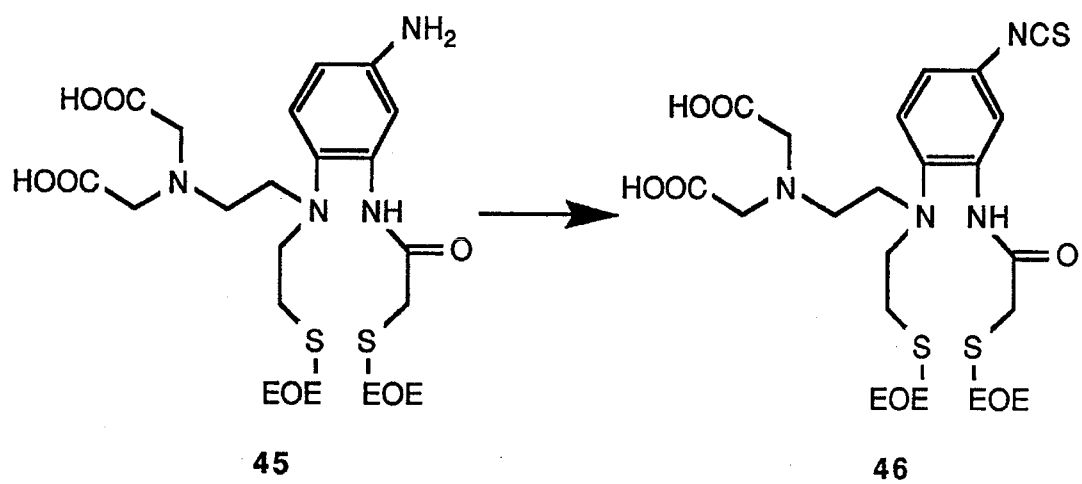

Synthesis of a diamidodimercapto bifunctional anchimeric chelate having an aromatic bridge 3-(β-S-ethoxyethyl)-acetamido-4-N-(β-S-1-ethoxyethyl)ethyl-N-(N',N'-dicarboxymethyl)-aminoethyl phenylisothiocyanate The following synthesis is best understood by referring to FIGS. 4a and 4b.

S-1-ethoxyethyl-N-β-dimethoxyethyl-mercaptoethylamine 39: A solution of S-ethoxyethyl-O-mesyl-mercaptoethanol 18 (1 mmol) (see EXAMPLE II for procedure) is stirred with aminoacetaldehyde dimethyl acetal at ambient temperature for 5–6 hours. The solution is diluted with saturated bicarbonate, extracted with methylene chloride. The combined organic extracts are washed with brine, dried over anhydrous sodium sulfate and evaporated in vacuo to give 39, which is purified by silica gel flash chromatography.

3-(β-S-1-ethoxyethyl)-acetamido-4-chloronitrobenzene 41: To a solution of 2-chloro-4-nitroaniline 40 (1 mmol) in 10 mL of anhydrous dimethylformamide, 1.1 mmol of S-(1-ethoxyethyl)mercaptoacetic acid succinimidate ester 8 (see EXAMPLE II) is added and the mixture is stirred for 6–8 hours at ambient temperature. The solvent is removed in vacuo, and water is added to the residue. The mixture is extracted with ethyl acetate, washed with water, dried over anhydrous sodium sulfate and evaporated to give 41.

3-(β-S-1-ethoxyethyl)-acetamido-4-N-(β-S-1-ethoxyethyl)ethyl-N-(β,β-dimethoxy)-ethyl nitrobenzene 42: An equimolar amount of a mixture of 3-(β-S-ethoxyethyl)-acetamido-4-chloronitrobenzene 41 and S-ethoxyethyl-N-β-dimethoxyethyl-mercaptoethylamine 39 heated in a mixture of anhydrous dimethylformamide for a period of 4–5 hours. The solvent is removed in vacuo and the residue is suspended in water. The solution is rendered alkaline with 1N sodium bicarbonate and extracted with methylene chloride. The organic layer is dried with anhydrous sodium sulfate and evaporated to give the product 42.

3-(β-S-1-ethoxyethyl)-acetamido-4-N-(β-S-ethoxyethyl)ethyl-N-(N',N'-dicarbomethoxymethyl)aminoethyl nitrobenzene 43:

(i) The above product (1 mmol) is treated with 5 mL of glacial acetic acid containing 1 mL 2N HCl and stirred at room temperature for 4–5 hours and evaporated to dryness. The residue is dissolved in ethyl acetate and washed with water. The organic layer is dried and evaporated to give the formyl intermediate.

(ii) The formyl intermediate is dissolved in 10 mL of anhydrous tetrahydrofuran and cooled to 0° C. To this a solution of an equimolar amount of iminodiacetic acid dimethyl ester in tetrahydrofuran is added. After stirring for 30 minutes at this temperature, 3–5 equivalents of sodium cyanoborohydride is added in portions. The mixture is stirred for another 2 hours and allowed to come to room temperature. The solvent is removed in vacuo, and the residue is dissolved in ethyl acetate. The organic layer is washed with water, dried, evaporated, and purified by silica gel chromatography to give product 43.

3-(β-S-ethoxyethyl)-acetamido-4-N-(β-S-ethoxyethyl)ethyl-N-(N',N'-dicarboxymethyl)aminoethyl nitrobenzene 44: A solution of 43 (1 mmol) is dissolved in 2 mL of ethanol and 3 mL of 1N NaOH and stirred at room temperature overnight. The solution is evaporated under reduced pressure and redissolved in 5 mL of water and acidified with 1N HCl to pH 3–4. The precipitated solid is filtered and dried to give 44.

3-(β-S-ethoxyethyl)-acetamido-4-N-(β-S-ethoxyethyl)ethyl-N-(N',N'-dicarboxymethyl)-aminoethyl aniline 45: The reduction is carried according to the procedure described in EXAMPLE II (reduction of 25 to the corresponding amino compound).

3-(β-S-ethoxyethyl)-acetamido-4-N-(β-S-ethoxyethyl)ethyl-N-(N',N'-dicarboxymethyl)-aminoethyl phenylisothiocyanate 46: The amino compound 45 is converted to the isothiocyanate in a procedure similar to that described in EXAMPLE II using thiocarbonyldiimidazole.

EXAMPLE V

Conjugation of Radiolabeled Chelate and Chelating Compound and Radiolabeling with Isotopes Radiolabeling of chelating compounds with (a) $^{99m}$Tc and (b) $^{186/188}$Re and conjugation with antibody (and fragments).

(a) To 100 µL of solution containing 5 mg of sodium gluconate and 0.1 mg of SnCl$_2$ in water, 500 µL of $^{99m}$TcO$_4^-$ (pertechnetate) is added. After incubation at room temperature for 10 minutes to form Tc-gluconate complex, 100 µg of a chelating compound (dissolved in i-propanol:acetic acid 90:10, a 1 mg/mL solution), 80 µL of 0.2N HCl, and 200 µL of i-propanol are added in that order. The chelating compound may be one of the four chelating compounds 11, 26, 38, or 46 prepared in EXAMPLES I to IV above. The reaction mixture is heated to 37° C. for 15 minutes, then cooled in ice for 5 minutes. To the above chelate, 100 µL of bicarbonate buffer is added, so that the pH of the solution is about 6.0. Next, 400 µL of an antibody (or fragment (5 mg/mL)) is added in the same buffer. The antibody is a monoclonal antibody (or fragments thereof) designated as NR-ML-05 (specific for melanoma cells), NR-LU-10 (a pancarcinoma monoclonal antibody), NR-CO-02 (specific for carcinoembryonic antigen (CEA) and colon carcinoma), or NR-CE-01 (anti-CEA). The reaction mixtures are incubated at room temperature for ½–1 hour as necessary. ITLC procedure (*Nuclear Medicine Technology and Techniques*, ed. Bernlet, D., Longan, J., and Wells, L., The C. V. Mosby Co., St. Louis, Mo., (1981); pp. 172–174) using 12% TCA is used to determine the percentage of chelate attached to the protein.

(b) The $^{188}$Re chelate of the ligand is prepared in a similar procedure. Sodium perrhenate (3 mL, 15 mCi, produced from a $^{188}$W/$^{188}$Re generator) is added to a vial containing a lyophilized mixture comprising citric acid, 75 mg; stannous chloride, 0.75 mg; gentisic acid, 0.25 mg and lactose, 100 mg. The vial is agitated gently to mix the contents, then incubated at room temperature for 10 minutes to form a $^{188}$Re-citrate complex. To a separate vial containing the 0.50 mg of the chelating agent, 0.50 mL of i-propanol is added and the vial is agitated for 2 minutes to completely dissolve the compound. Then 0.3 mL of this solution is transferred to the vial containing the Re-citrate complex. The reaction mixture is heated at 37° C. for 15 minutes, then cooled in ice for 5 minutes. The incubation with antibody (or its fragments) is carried out exactly as described in procedure (a) above using appropriate volume of bicarbonate buffer.

In both cases, the final purification of the antibody-chelate conjugate is achieved by passing the conjugate through a Sephadex-G$_{25}$ or a QAE-column. The purity of the conjugate is usually over 97% before administration to test animals and to humans.

Preparation of antibody-chelating compound conjugate followed by labeling with $^{99m}$Tc and $^{188}$Re:

Preparation of the conjugate: The antibody conjugation reaction is contained in a final volume of 4 mL: 0.1 mg (62 µmol) of the chelating compound, 1.1 mg of the monoclonal antibody (IgG, 7.3×10$^{-9}$ moles), 1–2 mL of distilled dimethylformamide (if necessary to solubilize the chelating compound), 0.05M of borate or 0.5M bicarbonate buffer at pH 8.5. After stirring for 90 minutes at room temperature, 4.4 mL of 5N sodium chloride is added. After additional 30 minutes, the reaction mixture is centrifuged to remove any particulates and the supernatant fractioned by gel filtration column chromatography. The column eluent is monitored at 280 nm and the fractions containing monomeric antibody conjugate are pooled and concentrated in an Amicon stirred cell (30,000 molecular weight cutoff).

(i) Technetium-99m labeling of antibody chelating compound conjugate with $^{99m}$Tc-tartrate.

Stannous tartrate kits are prepared from degassed solutions of 0.5 mL disodium tartrate (150 mg/mL) and 0.1 mL stannous chloride (1.0 mg/mL in ethanol) in an evacuated vial under nitrogen atmosphere. To a stannous tartrate kit, sodium pertechnetate 0.5 mL (about 15 mCi) is added and heated at 50° C. for 10–15 minutes. After cooling to room temperature, quality control for $^{99m}$Tc tartrate and insoluble $^{99m}$Tc is carried out on Gelman ITLC using methyl ethyl ketone and 0.01M sodium tartrate pH 7.0 eluants, respectively. $^{99m}$Tc tartrate formation is typically 98–99% with soluble $^{99m}$Tc values ranging from 0.1 to 0.2%.

In an evacuated vial, 100 µL saline, 200 µL of sodium phosphate (0.2M, pH 8.0) and 200 µL of antibody-chelating compound conjugate (1.9 mg/mL) are added successively. Immediately after adding the conjugate, 250 µL of $^{99m}$Tc tartrate (about 3 to 5 mCi) is added and heated at 37° C. for 1 hour. Percent technetium bound to protein and the formation of pertechnetate are determined by ITLC using 50% MeOH:10% ammonium acetate (1:1) and 1-butanol eluents, respectively.

(ii) Rhenium-188 labeling of antibody-chelating compound conjugate with Re-citrate.

The $^{188}$Re chelate is prepared in a similar procedure. Sodium perrhenate (3 mL, 15 mCi, produced from a $^{188}$W/$^{188}$Re generator) is added to a vial containing a lyophilized mixture comprising citric acid, 75 mg; stannous chloride, 0.75 mg; gentisic acid, 0.25 mg and lactose, 100 mg. The vial is agitated gently to mix the contents, then incubated at room temperature for 10 minutes to form a $^{188}$Re-citrate complex. The reaction mixture is heated at 75° C. for 15 minutes, then cooled in Ice for 5 minutes to prepare the Re-citrate complex for labeling of the conjugate.

Labeling of the conjugate is carried out in a similar procedure described for Tc in (i).

EXAMPLE VI

Diagnostic and Therapeutic Kits (A) Diagnostic Kit.

(i) Pre-Formed Approach

A diagnostic kit containing reagents for preparation of a $^{99m}$Tc-radiolabeled protein conjugate is used as follows. The procedures are conducted under conditions which ensure the sterility of the product (e.g., sterile vials and sterilized reagents are used where possible, and reagents are transferred using sterile syringes). Proper shielding was used once the radioisotope is introduced.

One mL of sterile water for injection is added to a sterile vial containing a stannous gluconate complex (50 mg sodium gluconate and 1.2 mg stannous chloride dihydrate, available from Merck Frosst, Canada, in dry solid form) and the vial is gently agitated until the contents are dissolved. A sterile insulin syringe is used to inject 0.1 mL of the resulting stannous gluconate solution into an empty sterile vial. Sodium pertechnetate (0.75 mL, 75–100 mCi, from a $^{99}$Mo/$^{99}$Tc generator available from DuPont, Mediphysics, Mallinckrodt, or E. R. Squibb) is added, and the vial is agitated gently to mix the contents, then incubated at room temperature for 10 minutes to form a $^{99m}$Tc-gluconate complex. In an alternative procedure for providing the $^{99m}$Tc-gluconate exchange complex, the kit includes a vial containing a lyophilized preparation comprising 5 mg sodium gluconate, 0.12 mg stannous chloride dihydrate, about 0.1 mg gentisic acid as a stabilizer compound, and about 20 mg lactose as a filler compound. The amount of gentisic acid may vary, with the stabilizing effect generally increasing up to about 0.1 mg. Interference with the desired reactions may occur when about 0.2 mg or more gentisic acid is added. The amount of lactose also may vary, with amounts between 20 and 100 mg, for example, being effective in aiding lyophilization. Addition of stabilizer and a filler compound is especially important when the vial contained these relatively small amounts of sodium gluconate and stannous chloride (compared to the alternative embodiment above). One mL of sodium pertechnetate (about 100 mCi) is added directly to the lyophilized preparation. The vial is agitated gently to mix the contents, then incubated as described above to form the $^{99m}$Tc-gluconate complex.

A separate vial containing 0.3 mg of a chelating compound of the present invention in dry solid form is prepared by dispensing a solution of 0.3 mg chelating agent in i-propanol into the vial, then removing the solvent under N$_2$ gas, and the resulting vial containing the chelating compound is provided in the kit. To this vial is then added 0.87 mL of 100% i-propanol, and the vial is gently shaken for about 2 minutes to completely dissolve the chelating agent. Next, 0.58 mL of this solution of the chelating agent is transferred to a vial containing 0.16 mL of glacial acetic acid/0.2N HCl (2.14), and the vial is gently agitated. Of this acidified solution, 0.5 mL is transferred to the vial containing the $^{99m}$Tc-gluconate complex, described above. After gentle agitation to mix, the vial is incubated in a 37° C. water bath for 15 minutes, then immediately transferred to a 0° C. ice bath for 2 minutes.

To a separate vial containing 10 mg of the Fab fragment of a monoclonal antibody in 0.5 mL of phosphate-buffered saline, is added 0.37 mL of 1.0M sodium bicarbonate buffer, pH 10.0. The Fab fragment is generated by treating the monoclonal antibody with papain according to conventional techniques. The vial is then gently agitated.

The vial containing the acidified solution of the $^{99m}$Tc-labeled chelate (see above) is removed from the ice bath, 0.1 mL of the sodium bicarbonate buffer is added, and the vial is agitated to mix. Immediately, the buffered antibody solution (above) is added, gently agitated to mix and incubated at room temperature for 20 minutes to allow conjugation of the radiolabeled chelate to the antibody.

A column containing an union exchanger, either DEAE-Sephadex or QAE-Sephadex, is used to purify the conjugate. The column is prepared under aseptic conditions as follows. Five 1 mL QAE-Sephadex columns are connected end-to-end to form a single column. Alternatively, a single 5 mL QAE-Sephadex column may be used. The column is washed with 5 mL of 37 mM sodium phosphate buffer, pH 6.8. A 1.2µ filter (available from Millipore) is attached to the column, and a 0.2µ filter is attached to the 1.2µ filter. A 22-gauge sterile, nonpyrogenic needle was attached to the 0.2µ filter.

The reaction mixture is drawn up into a 3 mL or 5 mL syringe, and any air bubbles are removed from the solution. After removal of the needle, the syringe is connected to the QAE-Sephadex column on the end opposite the filters. The needle cap is removed from the 22-gauge needle attached to the filter end of the column and the needle tip is inserted into a sterile, nonpyrogenic test tube. Slowly, over 2 minutes, the reaction mixture is injected into the column. The eluant collected in the test tube is discarded. The now empty syringe on top of the column is replaced with a 5 mL syringe containing 5 mL of 75 mM (0.45%) sodium chloride solution (from which air bubbles had been removed). The needle at the other end of the column is inserted aseptically into a sterile, nonpyrogenic 10 mL serum vial. Slowly, over 2 minutes, the NaCl solution is injected into the column, and the eluent is collected in the serum vial.

The total radioactivity in the serum vial is measured using a dose calibrator. The yield of the radiolabeled antibody is normally in the 60% range. The contents of the serum vial are drawn up into a sterile, pyrogen-free, 30 cc syringe and diluted to a total volume of 30 mL with sterile 0.9% NaCl for injection into a human patient. A quality control test is normally performed on a 0.01 mL aliquot before injection by instant thin layer chromatography.

If the radiochemical purity is less than 85%, the material should not be injected into a human patient. Using this procedure, radiochemical purities generally range from about 90% to 99%. The total amount of radioactivity also is measured prior to injection. In general, from 10 to 30 mCi will be administered to a human patient.

Prior to administering the radiolabeled Fab fragment (the diagnostic radiolabeled antibody fragment), an irrelevant antibody and an unlabeled specific antibody may be administered to the patient to improve the diagnostic images, as described above. The irrelevant antibody and the unlabeled specific antibody, are provided in the kit in separate vials.

The entire 30 mL sample containing the radiolabeled antibody fragment is administered to a patient by intravenous infusion. The infusion is completed in from about 5 minutes to about 15 minutes. The antibody fragment concentration in the sample is 0.33 mg/mL.

(ii) Post-Formed Approach

Stannous tartrate kits are prepared from degassed solutions of 0.5 mL disodium tartrate (150 mg/mL) and 0.1 mL stannous chloride (1.0 mg/mL in ethanol) in an evacuated vial under nitrogen atmosphere. To a stannous tartrate kit, sodium pertechnetate 0.5 mL (about 15 mCi) is added and heated at 50° C. for 10–15 minutes. After cooling to room temperature, quality control for $^{99m}$Tc-tartrate and insoluble $^{99m}$Tc is carried out on Gelman ITLC using methyl ethyl ketone and 0.01M sodium tartrate pH 7.0 eluents, respectively. $^{99m}$Tc-tartrate formation is typically 98–99% with soluble $^{99m}$Tc values ranging from 0.1 to 0.2%.

In an evacuated vial, 100 µL saline, 200 µL of sodium phosphate (0.2M, pH 8.0) and 200 µL of antibody-chelating compound conjugate (1.9 mg/mL) are added successively. Immediately after adding the conjugate, 250 µL of $^{99m}$Tc-tartrate (about 3 to 5 mCi is added and heated at 37° C. for 1 hour. Percent technetium bound to protein and the formation of pertechnetate are determined by ITLC using 50% MeOH:10% ammonium acetate (1:1) and 1-butanol eluants, respectively.

(B) Therapeutic Kit (i) Pre-Formed Approach

The $^{188}$Re chelate is prepared in a similar procedure. Sodium perrhenate (3 mL, 15 mCi, produced from a $^{188}$W/$^{188}$Re generator) is added to a vial containing a lyophilized mixture comprising citric acid, 75 mg; stannous chloride, 0.75 mg; gentisic acid, 0.25 mg and lactose, 100 mg. The vial is agitated gently to mix the contents, then incubated at 75° C. for 15 minutes and cooled to room temperature to form $^{188}$Re-citrate complex. To a separate vial containing the 0.50 mg of the chelating agent, 0.50 mL of i-propanol is added and the vial is agitated for 2 minutes to completely dissolve the compound. Then 0.3 mL of this solution is transferred to the vial containing the Re-citrate complex, and incubated at room temperature for about 1 hour to produce the desired $^{188}$Re-chelate.

A column containing a $C_{18}$ reversed phase low-pressure material (Baker $C_{18}$ cartridges) is used to purify the $^{188}$Re-labeled chelate. After conditioning of the cartridge with ethanol and water, the sample is loaded and washed with three times 2 mL of water and three times 2 mL of 20% ethanol/0.01M phosphate buffer. The column is then dried in vacuo and eluted with two times 1.0 mL acetonitrile.

The chelate is then conjugated to a Fab fragment of a monoclonal antibody. A buffered solution of the antibody fragment (5 mg/mL, 0.5 mL) is added to the purified $^{188}$Re-labeled chelate, followed by 0.5 mL of 0.5M carbonate/bicarbonate buffer pH 9.50. The reaction is kept at room temperature for 15 minutes, then 25 mg of L-lysine, 0.1 mL, is added and the reaction is pursued at room temperature for 15 minutes more.

A column containing Sephadex-$G_{25}$ material is used to purify the $^{188}$Re-chelate-antibody conjugate. The reaction mixture is loaded on top of the column, and 1.2 mL aliquots are collected using PBS buffer to rinse the reaction vial and elute the $^{188}$Re conjugate in the third and fourth fractions. The purity of the $^{188}$Re conjugate is usually greater than 97%. The conjugate is then further diluted with PBS, and radioactivity is measured prior to injection into the test animals and human subjects.

(ii) Post-Formed Approach

Sodium perrhenate (3 mL, 15 mCi, produced from a $^{188}$W/$^{188}$Re generator) is added to a vial containing a lyophilized mixture comprising citric acid, 75 mg; stannous chloride, 0.75 mg; gentisic acid, 0.25 mg and lactose, 100 mg. The vial is agitated gently to mix the contents, then incubated at room temperature for 10 minutes to form a $^{188}$Re-citrate complex. The reaction mixture is heated at 75° C. for 15 minutes, then cooled in ice for 5 minutes to prepare the Re-citrate complex ready for labeling of the conjugate. Labeling of the ligand-antibody conjugate is carried out in a procedure similar to procedure A(ii).

EXAMPLE VII

Imaging of Tumors in Humans

Antibody fragments radiolabeled with $^{99m}$Tc according to the method of the invention are injected into human patients to detect tumor sites (melanoma, lung, colon, etc. depending on the antibody used) within the body. The antibody fragments used are F(ab')$_2$, Fab' or Fab fragments of a monoclonal antibody specific for an antigen of the particular target tumor. The fragments were generated by standard techniques (i.e., pepsin treatment of the monoclonal antibody to generate the F(ab')$_2$ fragment, papain treatment of the monoclonal antibody to generate the Fab fragment, and treatment with a reducing agent such as dithiothreitol to generate the Fab' fragment).

Each patient receives a $^{99m}$Tc-chelate-antibody fragment conjugate prepared by the procedures described in EXAMPLE V above. The radiolabeled antibody fragments are purified, and a quality control test is performed, as described in EXAMPLE VI(A)(i). Approximately 40 minutes to 1 hour and 30 minutes prior to infusion of the radiolabeled antibody, each patient receives 41 to 50 mg of an irrelevant antibody in 12 to 20 mL of sterile saline by intravenous infusion. In addition, each patient receives 7.5 mg of a nonradiolabeled specific antibody in 20 mL of sterile saline by intravenous infusion either simultaneously with, or approximately 5 minutes prior to infusion of the radiolabeled specific antibody. The nonradiolabeled specific antibody is exactly the same as the one used for radiolabeling, generally in the form of a whole antibody or a F(ab')$_2$ fragment thereof. The irrelevant antibody is a monoclonal antibody designated NR2AD, which is a murine IgG$_{2a}$ immunoglobulin that is designed as an anti-idiotype that binds to a single patient's B-cell lymphoma and to no other human tissue.

Into each patient is injected 20 to 30 mL of sterile saline comprising the radiolabeled antibody fragment, by intravenous infusion. The patient receives from 11.4 mCi to about 30 mCi of $^{99m}$Tc radioisotope. The desired upper limit of radioisotope administered is 30 mCi, and the minimum for effective imaging of tumors is generally about 10 mCi. The total amount of protein in the administered solutions ranges from 2.5 mgs to 10 mgs. Imaging by gamma camera is performed at various timepoints, including a baseline image: immediately following infusion of the radiolabeled antibody and at timepoints less than 20 hours post-infusion such that "background" has substantially cleared but the radionuclide is still at an imageable level. The percentage of the total injected dose of radioactivity (in cpm) which had localized in each of the various tissue types sampled are calculated. The ratio of the radioactivity found in tumor sites to the radioactivity found in the other types of tissue are also calculated. The value for "percent injected dose per mg" for the tumor tissue in a particular patient is divided by the value for "percent injected dose per mg" for each nontumor tissue sample extracted from the patient to give the tumor/tissue ratio for each nontumor tissue sample.

EXAMPLE VIII

Biodistribution Studies

Biodistribution Studies in Mice for $^{99m}$Tc-labeled and $^{188}$Re-labeled Monoclonal Antibody Fragments Antibody fragments radiolabeled with $^{99m}$Tc or $^{188}$Re are injected into tumor-bearing mice, and biodistribution of the radionuclide metal-chelate-protein conjugate is analyzed 20 hours after injection according to the method of Hwang, et al., *Cancer Res.*, 45:4150–4155 (1985). The antibody fragment is a Fab fragment of one of the above-described monoclonal antibodies (NM-ML-05, NR-LU-10, NR-CO-02, or NR-CE-01). The data is collected in terms of the percentage of the injected radioactivity per gram of each specified tissue type and tumor/tissue ratio of injected radioactivity. The tissue types are as follows: tail; tumor; skin; muscle; bone; lung; liver; spleen; stomach; thyroid; kidney; and intestine. A high percentage of the injected radioactivity is localized at the tumor site in each mouse.

While the invention has been described in conjunction with preferred embodiments, one of ordinary skill after reading the foregoing specification will be able to effect various changes, substitutions of equivalents, and alterations to the subject matter set forth herein. Hence, the invention can be practiced in ways other than those specifically described herein. It is therefore intended that the protection granted by Letters Patent hereon be limited only by the appended claims and equivalents thereof.

The embodiments of the invention in which an exclusive property or privilege is claimed are defined as follows:

1. A conjugate comprising a protein, protein fragment or polypeptide bound to a chelating compound comprising a first site at which a complex of a radionuclide metal forms, a second site at which a chelate of the radionuclide metal forms, and a conjugation group adapted to bind the chelating compound to the protein, wherein said first site comprises two or more atoms selected from oxygen, nitrogen and phosphorous, said second site comprises a heteroatom chain containing at least one sulfur atom and at least two nitrogen atoms, and the complex formed at said first site has a faster rate of formation and a lower thermodynamic stability than said chelate formed at said second site, such that when a radionuclide metal is combined with said compound, the complex at the first site forms initially, and the radionuclide metal subsequently is transferred to the second site to form the chelate.

2. The conjugate of claim 1 wherein said protein is a monoclonal antibody or an antigen binding fragment thereof.

3. The conjugate of claim 2 wherein said monoclonal antibody binds cancer cells.

4. The conjugate of claim 1 wherein the radionuclide metal is transferred to the second site by incubating the compound after the complex has formed.

5. The conjugate of claim 4 wherein the compound is heated to a temperature between ambient temperature and about 37° C.

6. The conjugate of claim 1 wherein the first site comprises two or more atoms chosen from oxygen, nitrogen, and phosphorous in the form of an oxide, wherein said atoms interact with the radionuclide metal to form the complex.

7. The conjugate of claim 1 wherein the second site comprises a heteroatom chain containing at least four donor atoms chosen from sulfur, nitrogen, and oxygen, wherein coordinate covalent bonds form between each of said donor atoms and the radionuclide metal to form the chelate.

8. The conjugate of claim 7 wherein said donor atoms include at least one divalent sulfur atom and at least two nitrogen atoms, the sulfur atom being positioned at one terminus of the heteroatom chain, and from six to seven carbon atoms positioned so that at least two carbon atoms are positioned between any two of the donor atoms.

9. The conjugate of claim 8 wherein said donor atoms are two nitrogen atoms and two sulfur atoms.

10. The conjugate of claim 8 wherein said donor atoms are three nitrogen atoms and one sulfur atom.

11. The conjugate of claim 8 wherein at least one sulfur donor atom, together with a protective group attached thereto, defines a hemithioacetal group.

12. The conjugate of claim 1 wherein said first site is bound to said second site through a flexible divalent linker.

13. The conjugate of claim 12 wherein said linker comprises from two to six methylene groups in a chain.

14. The conjugate of claim 1 which further comprises a conjugation group which binds the protein to the chelating compound, wherein the conjugation group is attached through a spacer to a carbon or a nitrogen atom of the chelating compound.

15. The conjugate of claim 1 represented by the structural formula:

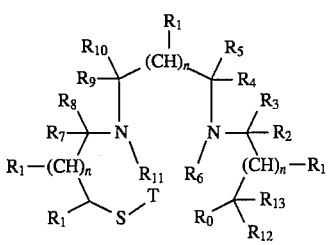

1) wherein:
   a) T is a sulfur-protecting group;
   b) $R_0$ is S—T, $O^-$, =O or

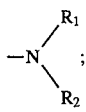

c) the R groups designated $R_1$ through $R_{11}$ are independently selected from COOH, $R_{14}$ and $R_{15}$—Z—Pr, wherein any two of said R groups, when bonded to the same carbon atom, may be taken together to form an oxo group, with the provisos that:
      i) $R_7$ and $R_8$ taken together, and $R_9$ and $R_{10}$ taken together, are not both simultaneously oxo;
      ii) $R_2$ and $R_3$ taken together, and $R_4$ and $R_5$ taken together, are not both simultaneously oxo;
      iii) $R_4$, $R_5$, $R_9$, and $R_{10}$ may all be taken together to form a hydrocarbon ring;
      iv) $R_6$ is hydrogen when either $R_2$ and $R_3$ or $R_4$ and $R_5$ represent an oxo group;
      v) $R_{11}$ is hydrogen when either $R_7$ and $R_8$ or $R_9$ and $R_{10}$ represent an oxo group;
      vi) each of $R_7$, $R_8$, $R_9$, and $R_{10}$ are hydrogen when $R_{11}$ is $R_{15}$—Z—Pr or $R_{16}$;
      vii) each of $R_2$, $R_3$, $R_4$, and $R_5$ are hydrogen when $R_6$ is $R_{15}$—Z—Pr or $R_{16}$;
      viii) $R_6$ and $R_{11}$ cannot be COOH;
   d) $R_{12}$ and $R_{13}$ are (1) independently $R_{14}$ or $R_{15}$—Z—Pr when $R_0$ is either S—T or

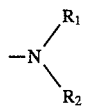

or (2) taken together to form oxo when $R_0$ is either $O^-$, =O or

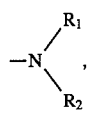

with the proviso that when $R_{12}$ and $R_{13}$ are oxo and $R_0$ is

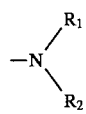

and one of these two $R_1$ groups is $R_{15}$—Z—Pr or $R_{16}$, the other $R_1$ group is hydrogen;
   e) $R_{14}$ is hydrogen, lower alkyl, or $R_{16}$;
   f) n is 0 or 1 provided that n equals 1 not more than once;
   g) $R_{15}$ is a divalent spacer selected from substituted or unsubstituted lower alkyl, which may additionally comprise one or more groups selected from —O—, —NH—, —NR—, —CO—, —$CO_2$—, —CONH—, —S—, —SO—, —$SO_2$—, —$CO_2$NH—, and —$SO_2$NR—, where R is selected from $C_1$-$C_3$ alkyl;
   h) Z is a functional group suitable for reacting with a protein, protein fragment, or polypeptide under conditions that preserve biological activity of the protein, protein fragment, or polypeptide;
   i) Pr is a protein, protein fragment or polypeptide;
2) wherein said compound comprises at least one substituent $R_{15}$—Z—Pr; and
3) wherein at least one of the groups $R_1$-$R_{14}$ is substituent $R_{16}$ having the formula:

wherein:
   a) one or more $R_{17}$ groups are bonded to any carbon or nitrogen atom and are selected from the group hydrogen, lower alkyl, or $R_{15}$—Z—Pr;
   b) X is a radical selected from the group consisting of fully substituted carbon, nitrogen, oxygen, $sp^2$ or sp carbon, or amide or imide nitrogen;
   c) p in an integer, 2, 3, 4, 5, or 6 provided that:
      i) when p is 2 or 3, X is fully substituted carbon;
      ii) when p is 4, X is fully substituted carbon, nitrogen, or oxygen, further provided that at least three radicals X are fully substituted carbon;
      iii) when p is 5 or 6, at least three radicals X are fully substituted carbon and further provided that only one radical X may be $sp^2$ or sp carbon, amide or imide nitrogen; and
   d) Q represents the first site.

16. The conjugate of claim 15 wherein Q is selected from the group consisting of iminodiacetate, alkyl phosphonate, alkyl diphosphonate, N-glycine, aminoalkylpolyacetate, alkylhydroxycarboxylate, polyhydroxyaminoalkanes, alkylaminohydroxycarboxylate, and alkyldihydroxydicarboxylate.

17. The conjugate of claim 15 wherein Q is selected from the group consisting of polyhydroxycarboxylates, gluconate, tartrate, alkyl phosphonate, alkyl, disphosphonate, gluconamide, N-glycine, N-3-aminopropanoate, α-hydroxy acids, α-hydroxy-β-amino acids, α-hydroxy-α-amino acids, deoxyamino uronic acids, β-diketones or enol equivalents thereof,

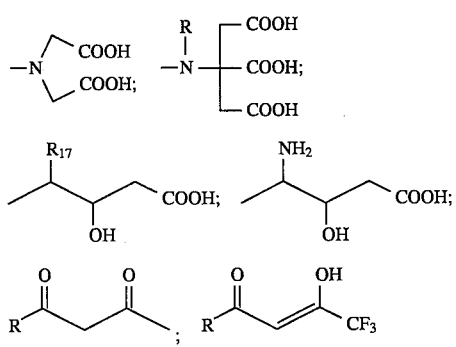

and derivatives thereof; wherein R is $C_1$-$C_5$ lower alkyl and $R_{17}$ is hydrogen, lower alkyl or $R_{15}$—Z—Pr, wherein $R_{15}$ is a divalent spacer and Z is a group reactive with a protein.

18. The conjugate of claim 15 wherein Z is selected from the group consisting of active esters, isothiocyanate groups, maleimide groups, amine groups, and halomethyl ketones.

19. The conjugate of claim 15 wherein one or more substituents T is a protecting group which, when taken together with the sulfur atom to which it is attached, defines a hemithioacetal.

20. The conjugate of claim 19 wherein said hemithioacetal is selected from the group consisting of ethoxyethyl, tetrahydropyranyl, 2-methyl tetrahydropyranyl, 6-carboxy tetrahydropyranyl, tetrahydrofuranyl, and 2-methyl tetrahydrofuranyl.

21. The conjugate of claim 15 wherein the compound is represented by one of the structural Formulae II–XIV:

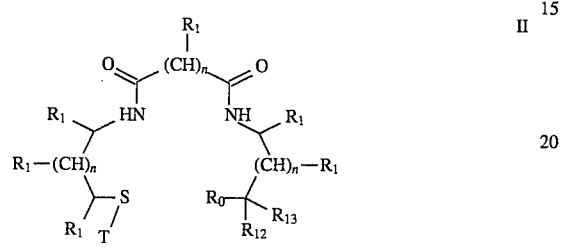

II

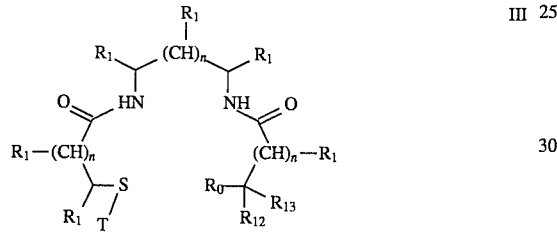

III

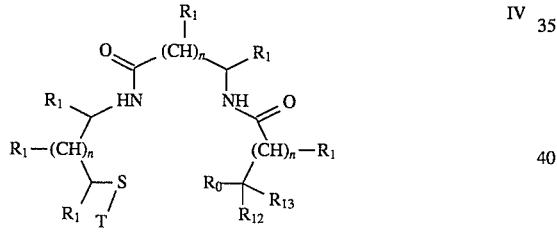

IV

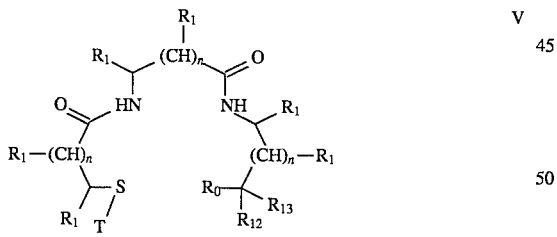

V

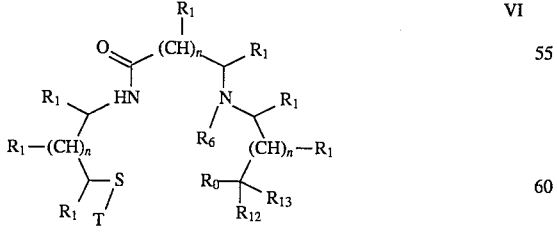

VI

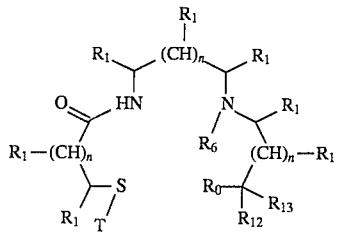

VII

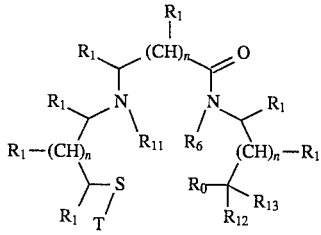

VIII

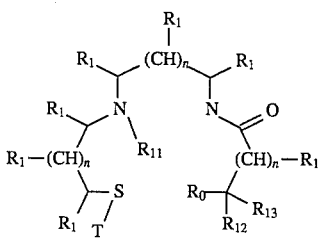

IX

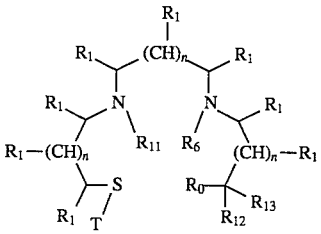

X

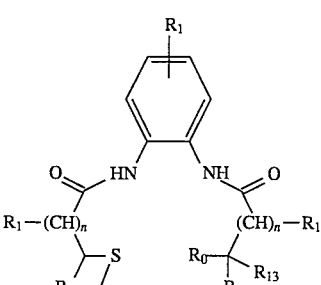

XI

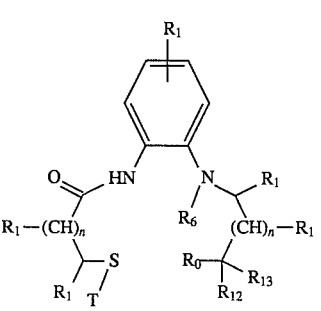

XII

-continued

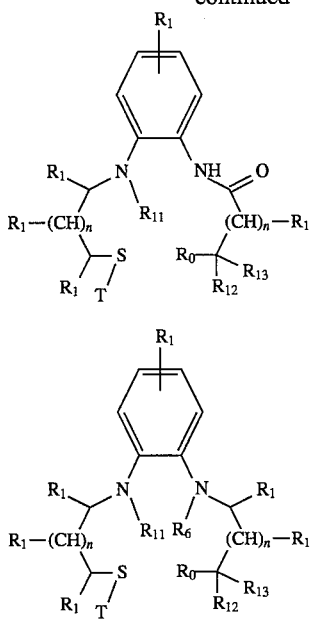

wherein:
a) when $R_6$ is $R_{16}$ or $R_{15}$—Z—Pr, each $R_1$ group attached to a carbon atom adjacent to —N—$R_6$ is hydrogen; and, b) when $R_{11}$ is $R_{16}$ or $R_{15}$—Z—Pr, each $R_1$ group attached to a carbon atom adjacent to —N—$R_{11}$ is hydrogen.

22. The conjugate of claim 15 wherein the compound has the following structural formula:

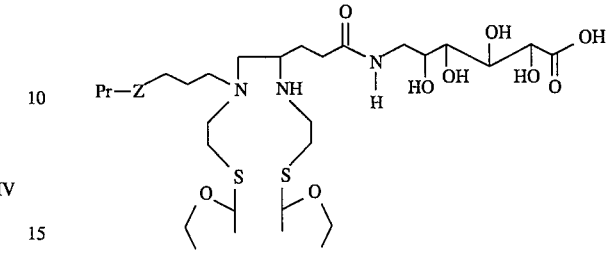

wherein Z represents an active ester group or an isothiocyanate group.

23. A conjugate of claim 1 which further comprises a radionuclide metal chelated with the first or second site of the chelating compound.

24. The conjugate of claim 23 wherein the radionuclide metal is selected from the group consisting of $^{99m}$Tc, $^{188}$Re, $^{186}$Re, $^{67}$Cu, $^{64}$Cu, $^{212}$Pb, $^{212}$Bi, $^{105}$Rd, $^{97}$Ru, and $^{109}$Pd.

25. The conjugate of claim 24 wherein the radionuclide metal is selected from $^{99m}$Tc, $^{188}$Re, and $^{186}$Re.

* * * * *

UNITED STATES PATENT AND TRADEMARK OFFICE
CERTIFICATE OF CORRECTION

PATENT NO. : 5,606,028
DATED : February 25, 1997
INVENTOR(S) : A.R. Fritzberg et al.

It is certified that error appears in the above-identified patent and that said Letters Patent is hereby corrected as shown below:

| COLUMN | LINE | ERROR |
|---|---|---|
| [56] Pg. 1, col. 1 | Refs. Cited (U.S. Pats.) | Insert the following reference: --5,175,343 12/1992 Fritzberg et al. 560/45-- |
| [56] Pg. 1, col. 2 | Refs. Cited (Other Publs., Item 7) | ""monoclonal" should read --"Monoclonal-- |
| [56] Pg. 2, col. 1 | Refs. Cited (Other Publs., Item 12) | "*Med,*" should read --*Med.,*-- |
| [56] Pg. 2, col. 1 | Refs. Cited (Other Publs., Item 16) | "et al," should read --et al.,-- |
| [56] Pg. 2, col. 1 | Refs. Cited (Other Publs., Item 16) | "Chem, Commun.," should read --Chem. Commun.,-- |
| [56] Pg. 2, col. 2 | Refs. Cited (Other Publs., Item 18) | "*Med,*" should read --*Med.,*-- |
| [56] Pg. 2, col. 2 | Refs. Cited (Other Publs., Item 20) | "ethyphenylglyoxal" should read --ethylphenylglyoxal-- |

Page 1 of 8

UNITED STATES PATENT AND TRADEMARK OFFICE
CERTIFICATE OF CORRECTION

PATENT NO. : 5,606,028
DATED : February 25, 1997
INVENTOR(S) : A.R. Fritzberg et al.

It is certified that error appears in the above-identified patent and that said Letters Patent is hereby corrected as shown below:

| COLUMN | LINE | ERROR |
|---|---|---|
| [56] Pg. 2, col. 2 | Refs. Cited (Other Publs., Item 20) | After "*Med*" insert --.-- |
| [56] Pg. 2, col. 2 | Refs. Cited (Other Publs., Item 26) | "*Med*," should read --*Med.,*-- |
| 1 | 33 | "3,987,1571" should read --3,987,157;-- |
| 2 | 4 | After "such" insert --as-- |
| 2 | 15 | "(TcO$_4$)" should read --(TcO$_4^-$)-- |
| 10 | 32 | "Klofutar et el.," should read --Klofutar et al.,-- |
| 10 | 34 | "Fawwaz et el.," should read --Fawwaz et al.,-- |
| 10 | 36 | "Kozah et el.," should read --Kozah et al.,-- |
| 10 | 37 | "*Aced.*" should read --*Acad.*-- |

UNITED STATES PATENT AND TRADEMARK OFFICE
CERTIFICATE OF CORRECTION

PATENT NO. : 5,606,028
DATED : February 25, 1997
INVENTOR(S) : A.R. Fritzberg et al.

It is certified that error appears in the above-identified patent and that said Letters Patent is hereby corrected as shown below:

| COLUMN | LINE | ERROR |
|---|---|---|
| 13 | 48-57 | In Formula I, "$R_6$", leftmost occurance, should read --$R_8$--, so that the formula |

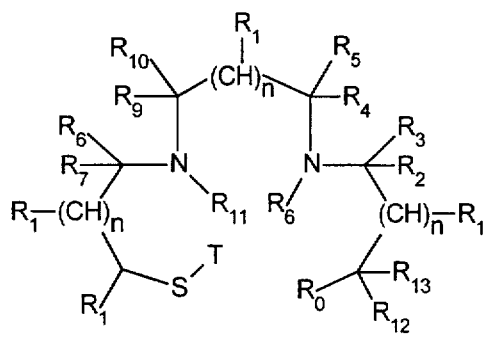

is corrected to read

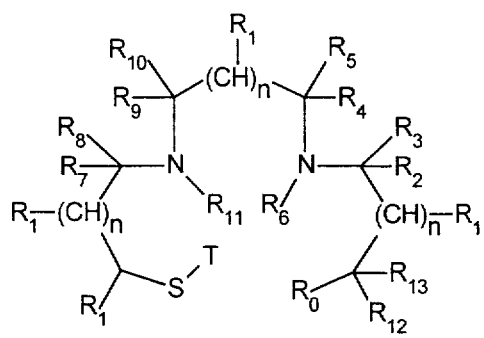

| | | |
|---|---|---|
| 13 | 67 | "R15-Z," should read --$R_{15}$-Z,-- |
| 15 | 1 | After "integer" delete "," |
| 15 | 40 | After "Formula" insert --I-- |
| 16 | 25 | "-$CH_2$-$CH_2$-$CH_2$-$CH_2$-$CH_2$$CH_2$-," should read ---$CH_2$-$CH_2$-$CH_2$-$CH_2$-$CH_2$-$CH_2$-,-- |

UNITED STATES PATENT AND TRADEMARK OFFICE
CERTIFICATE OF CORRECTION

PATENT NO. : 5,606,028
DATED : February 25, 1997
INVENTOR(S) : A.R. Fritzberg et al.

Page 4 of 8

It is certified that error appears in the above-identified patent and that said Letters Patent is hereby corrected as shown below:

| COLUMN | LINE | ERROR |
|---|---|---|
| 17 | 43-45 | In Formula VIII, "N-$R_6$" should read --NH--, so that the formula |

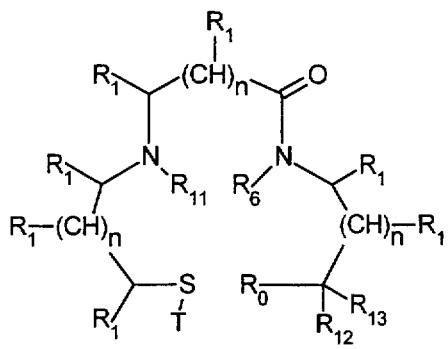 is corrected to read 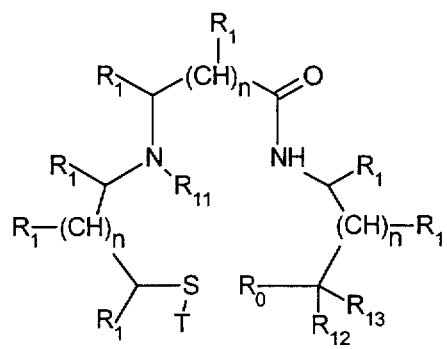

UNITED STATES PATENT AND TRADEMARK OFFICE
CERTIFICATE OF CORRECTION

PATENT NO. : 5,606,028
DATED : February 25, 1997
INVENTOR(S) : A.R. Fritzberg et al.

It is certified that error appears in the above-identified patent and that said Letters Patent is hereby corrected as shown below:

| COLUMN | LINE | ERROR |
|---|---|---|
| 18 | 11-18 | In Formula XI, "N-$R_6$" should read --NH--, so that the formula |

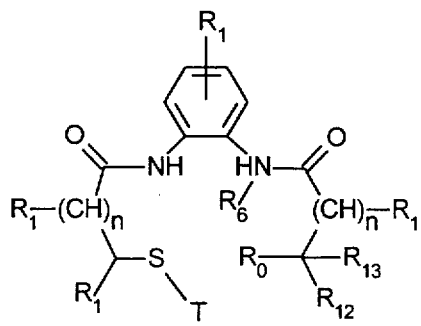

is corrected to read

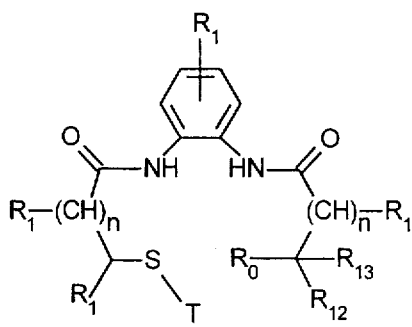

| | | |
|---|---|---|
| 19 | 3 | "Is" should read --is-- |
| 19 | 11 | "include-monoamino" should read --include monoamino-- |
| 24 | 18 | "Fe receptors" should read --Fc receptors-- |
| 25 | 51 | "($^{99m}TcO_4$)" should read --($^{99m}TcO_4^-$)-- |
| 26 | 33 | "In" should read --in-- |

UNITED STATES PATENT AND TRADEMARK OFFICE
CERTIFICATE OF CORRECTION

PATENT NO. : 5,606,028
DATED : February 25, 1997
INVENTOR(S) : A.R. Fritzberg et al.

It is certified that error appears in the above-identified patent and that said Letters Patent is hereby corrected as shown below:

| COLUMN | LINE | ERROR |
|---|---|---|
| 26 | 49 | "Invention" should read --invention-- |
| 26 | 50 | "In" should read --in-- |
| 26 | 66 | "0° - 5° C." should read --0° - -5° C.-- |
| 27 | 35 | "0° - 5° C.," should read --0° - -5° C.,-- |
| 27 | 40 | "0° - 5° C.)," should read --0° - -5° C.),-- |
| 30 | 1 | "-S-" should read ---β--- |
| 30 | 11 | "Is" should read --is-- |
| 30 | 55 | "butyldimethylsily" should read --butyldimethylsilyl-- |
| 30 | 67 | After "26" insert --:-- |
| 32 | 53 | "38.Deprotection" should read --38: Deprotection-- |
| 33 | 50 | Between "(N',N'-dicarboxymethyl)" and "aminoethyl" insert -- - -- |
| 34 | 30 | "Bernlet," should read --Bernier,-- |

UNITED STATES PATENT AND TRADEMARK OFFICE
CERTIFICATE OF CORRECTION

PATENT NO. : 5,606,028
DATED : February 25, 1997
INVENTOR(S) : A.R. Fritzberg et al.

It is certified that error appears in the above-identified patent and that said Letters Patent is hereby corrected as shown below:

| COLUMN | LINE | ERROR |
|---|---|---|
| 34 | 53 | "Sephadex-$G_{25}$" should read --Sephadex-G25-- |
| 35 | 38 | "lee" should read --ice-- |
| 36 | 2 | Begin a new paragraph with: "In an alternative . . ." |
| 36 | 32 | "(2.14)," should read --(2:14),-- |
| 36 | 52 | "union" should read --anion-- |
| 38 | 23 | "Sephadex-$G_{25}$" should read --Sephadex-G25-- |
| 38 | 42 | Begin a new paragraph with: "Labeling of the . . ." |
| 42 | 66-67 | After "$R_{15}$-Z-Pr" delete ", wherein $R_{15}$ is a divalent spacer and Z is a group reactive with a protein" |

UNITED STATES PATENT AND TRADEMARK OFFICE
CERTIFICATE OF CORRECTION

PATENT NO. : 5,606,028
DATED : February 25, 1997
INVENTOR(S) : A.R. Fritzberg et al.

It is certified that error appears in the above-indentified patent and that said Letters Patent is hereby corrected as shown below:

COLUMN  LINE  ERROR

44  14-17

In Formula VIII, "N-$R_6$" should read --NH--, so that the formula

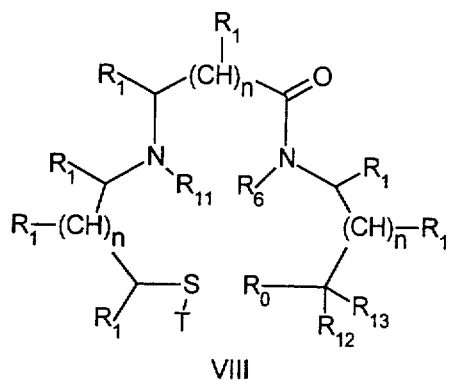

is corrected to read

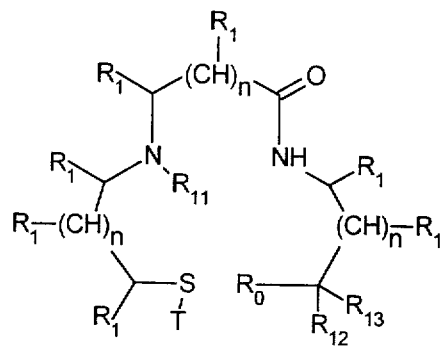

Signed and Sealed this

Tenth Day of March, 1998

Attest:

BRUCE LEHMAN

Attesting Officer    Commissioner of Patents and Trademarks